(12) United States Patent
Jiang et al.

(10) Patent No.: US 7,241,803 B2
(45) Date of Patent: Jul. 10, 2007

(54) COMPOUNDS FOR INHIBITION OF HIV INFECTION BY BLOCKING HIV ENTRY

(75) Inventors: Shibo Jiang, Fresh Meadows, NY (US); Asim Kumar Debnath, Fort Lee, NJ (US)

(73) Assignee: New York Blood Center, New York, NY (US)

( * ) Notice: Subject to any disclaimer, the term of this patent is extended or adjusted under 35 U.S.C. 154(b) by 441 days.

(21) Appl. No.: 10/706,027

(22) Filed: Nov. 12, 2003

(65) Prior Publication Data

US 2004/0116427 A1 Jun. 17, 2004

Related U.S. Application Data

(60) Provisional application No. 60/428,055, filed on Nov. 21, 2002.

(51) Int. Cl.
C07D 207/327 (2006.01)
A61K 31/402 (2006.01)
(52) U.S. Cl. ................. 514/427; 548/560; 548/563
(58) Field of Classification Search ........... 548/560, 548/563; 514/427
See application file for complete search history.

(56) References Cited

U.S. PATENT DOCUMENTS

| | | | | |
|---|---|---|---|---|
| 3,687,971 | A * | 8/1972 | Shen et al. | 548/563 |
| 3,717,659 | A * | 2/1973 | Sarett et al. | 548/563 |
| 4,339,457 | A | 7/1982 | Plummer et al. | |
| 5,627,203 | A * | 5/1997 | Rault et al. | 514/411 |
| 5,665,739 | A * | 9/1997 | Lang et al. | 514/345 |
| 5,824,691 | A * | 10/1998 | Kuno et al. | 514/335 |
| 6,596,497 | B1 | 7/2003 | Jiang et al. | |
| 2004/0180889 | A1* | 9/2004 | Suto et al. | 514/235.2 |

OTHER PUBLICATIONS

Fogassy et al., J. Chem. Soc., Perkin Transactions 1, 9, 1039-1043, Apr. 18, 2001.*
Jones et al., Journal of Medicinal Chemistry, 21911), 1100-1104, 1978.*
Sarett et al., Chemical Abstracts, 81:63478, 1974.*
Pedersen et al., New England Journal of Medicine, 322(25), 1757-1763, Jun. 21, 1990.*
Kweder et al., New England Journal of Medicine, 322(25), 1807-1809, Jun. 21, 1990.*
Chan, D. C., C. T. Chutkowski, and P. S. Kim. 1998. Evidence that a prominent cavity in the coiled coil of HIV type 1 gp41 is an attractive drug target. Proc. Natl. Acad. Sci. U S A 95:15613-15617.
Chan, D. C., D. Fass, J. M. Berger, and P. S. Kim. 1997. Core structure of gp41 from the HIV envelope glycoprotein. Cell 89:263-273.

Debnath, A. K., L. Radigan, and S. Jiang. 1999. Structure-based identification of small molecule antiviral compounds targeted to the gp41 core structure of the human immunodeficiency virus type 1. J. Med. Chem. 42:3203-3209.
Eckert, D. M., V. N. Malashkevich, L. H. Hong, P. A. Carr, and P. S. Kim . 1999. Inhibiting HIV-1 entry: discovery of D-peptide inhibitors that target the gp41 coiled-coil pocket. Cell 99:103-115.
Ernst, J. T., O. Kutzki, A. K. Debnath, S. Jiang, H. Lu, and A. D. Hamilton. 2002. Design of a Protein Surface Antagonist Based on alpha-Helix Mimicry: Inhibition of gp41 Assembly and Viral Fusion. Angew. Chem. Int. Ed Engl. 41:278-281.
Jiang, S. and A. K. Debnath. 2000. A salt bridge between an N-terminal coiled coil of gp41 and an antiviral agent targeted to the gp41 core is important for anti-HIV-1 activity. Biochem. Biophys. Res. Commun. 270:153-157.
Jiang, S., K. Lin, and M. Lu. 1998. A conformation-specific monoclonal antibody reacting with fusion-active gp41 from the HIV-1 envelope glycoprotein. J. Virol. 72:10213-10217.
Jiang, S., K. Lin, N. Strick, and A. R. Neurath. 1993. HIV-1 inhibition by a peptide. Nature 365:113.
Jiang, S., K. Lin, L. Zhang, and A. K. Debnath. 1999. A screening assay for antiviral compounds targeted to the HIV-1 gp41 core structure using a conformation-specific monoclonal antibody. J. Virol. Methods 80:85-96.
Jiang, S., Q. Zhao, and A. K. Debnath. 2002. Peptide and Non-peptide HIV Fusion Inhibitors. Curr. Pharm. Des. 8:563-580.
Lin, P. F., W. Blair, T. Wang, T. Spicer, Q. Guo, N. Zhou, Y. F. Gong, H. G. Wang, R. Rose, G. Yamanaka, B. Robinson, C. B. Li, R. Fridell, C. Deminie, G. Demers, Z. Yang, L. Zadjura, N. Meanwell, and R. Colonno. 2003. A small molecule HIV-1 inhibitor that targets the HIV-1 envelope and inhibits CD4 receptor binding. Proc. Natl. Acad. Sci. U. S. A 100:11013-11018.

(Continued)

*Primary Examiner*—Fiona T. Powers
(74) *Attorney, Agent, or Firm*—Law Offices of Albert Wai-Kit Chan, PLLC

(57) ABSTRACT

A group of compounds that inhibit HIV replication by blocking HIV entry was identified. Two representative compounds, designated NB-2 and NB-64, inhibited HIV replication (p24 production) with $IC_{50}$ values <0.5 µg/ml. It was proved that NB-2 and NB-64 are HIV entry inhibitors by targeting the HIV gp41 since: 1) they inhibited HIV-mediated cell fusion; 2) they inhibited HIV replication only when they were added to the cells less than one hour after virus addition; 3) they did not block the gp120-CD4 binding; 4) they did not interact with the coreceptor CXCR4 since they failed to block anti-CXCR4 antibody binding to CXCR4-expressing cells; 5) they blocked the formation of the gp41 core that is detected by sandwich enzyme linked immunosorbent assay (ELISA) using a conformation-specific MAb NC-1; 6) they inhibited the formation of the gp41 six-helix bundle revealed by fluorescence native-polyacrylamide gel electrophoresis (FN-PAGE); and 7) they blocked binding of D-peptide to the hydrophobic cavity within gp41 coiled coil domain, modeled by peptide IQN17. These results suggested that NB-2 and NB-64 may interact with the hydrophobic cavity and block the formation of the fusion-active gp41 coiled coil domain, resulting in inhibition of HIV-1 mediated membrane fusion and virus entry.

26 Claims, 8 Drawing Sheets

OTHER PUBLICATIONS

Figure 2:
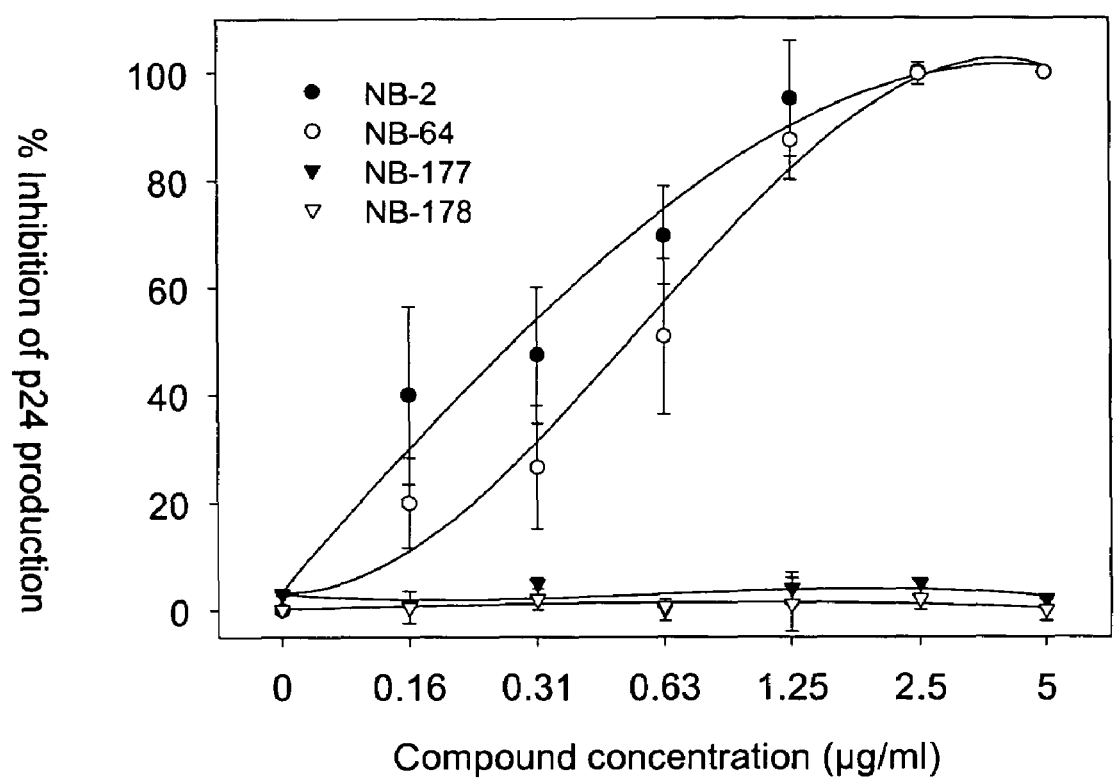

Liu, S., Q. Zhao, and S. Jiang. 2003. Determination of the HIV-1 gp41 postfusion conformation modeled by synthetic peptides: applicable for identification of the HIV-1 fusion inhibitors. Peptide in press.

Weissenhorn, W., A. Dessen, S. C. Harrison, J. J. Skehel, and D. C. Wiley. 1997. Atomic Structure of the Ectodomain from HIV-1 gp41. Nature 387:426-428.

Zhao, Q., J. T. Ernst, A. D. Hamilton, A. K. Debnath, and S. Jiang. 2002. XTT formazan widely used to detect cell viability inhibits HIV type 1 infection in vitro by targeting gp41. AIDS Res. Hum. Retroviruses 18:989-997.

PCT International Search Report for New York Blood Center, et al., Int'l Application No. PCT/US03/36359, Filed Nov. 12, 2003, Dated Jul. 14, 2004.

* cited by examiner

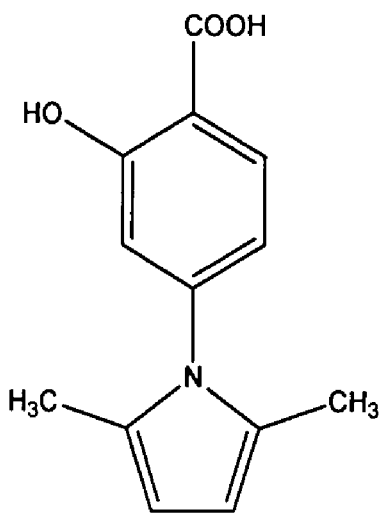
NB-2
MW: 231
ClogP: 4.28
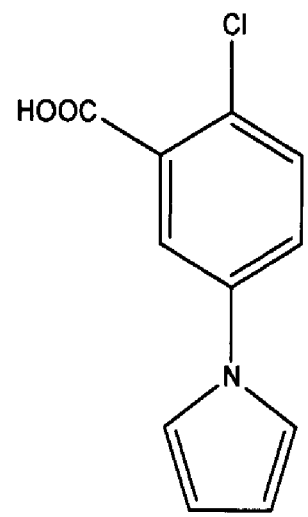
NB-64
MW: 222
ClogP: 3.15
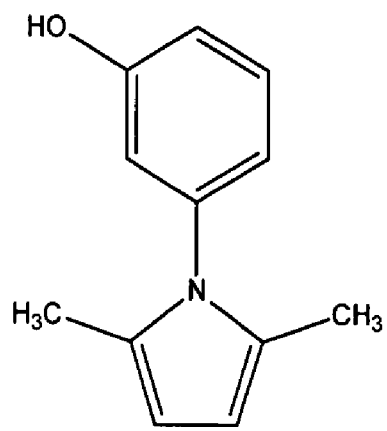
NB-177
MW: 187
ClogP: 3.75
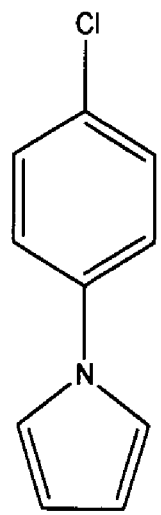
NB-178
MW: 178
ClogP: 3.86

Figure 4
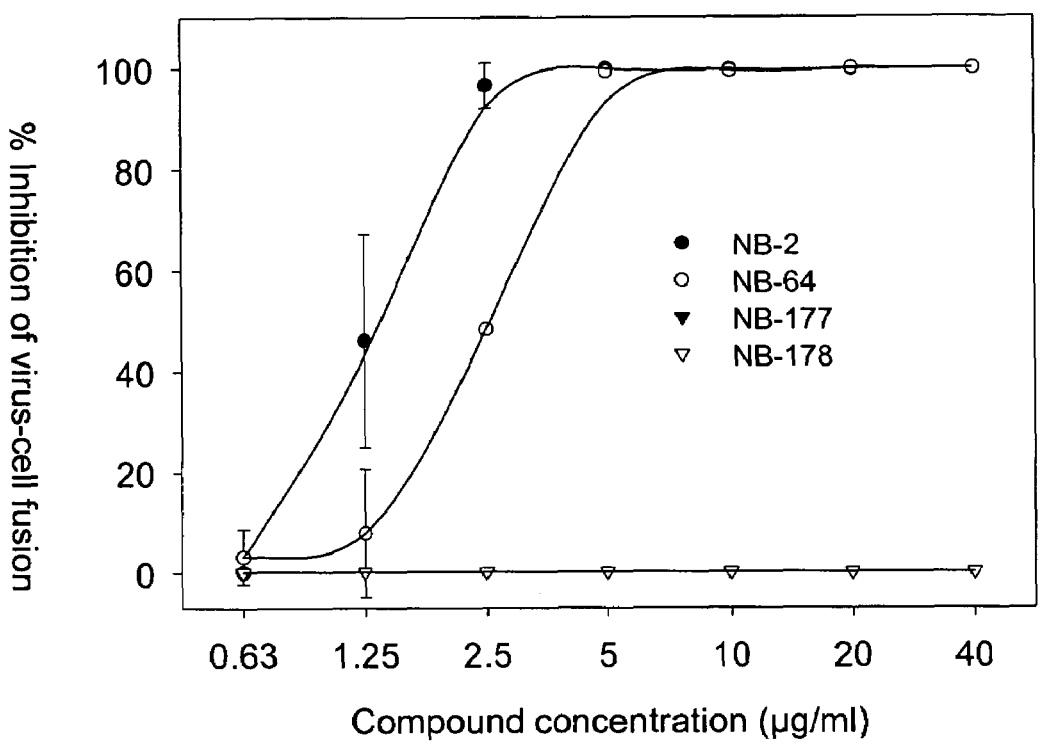
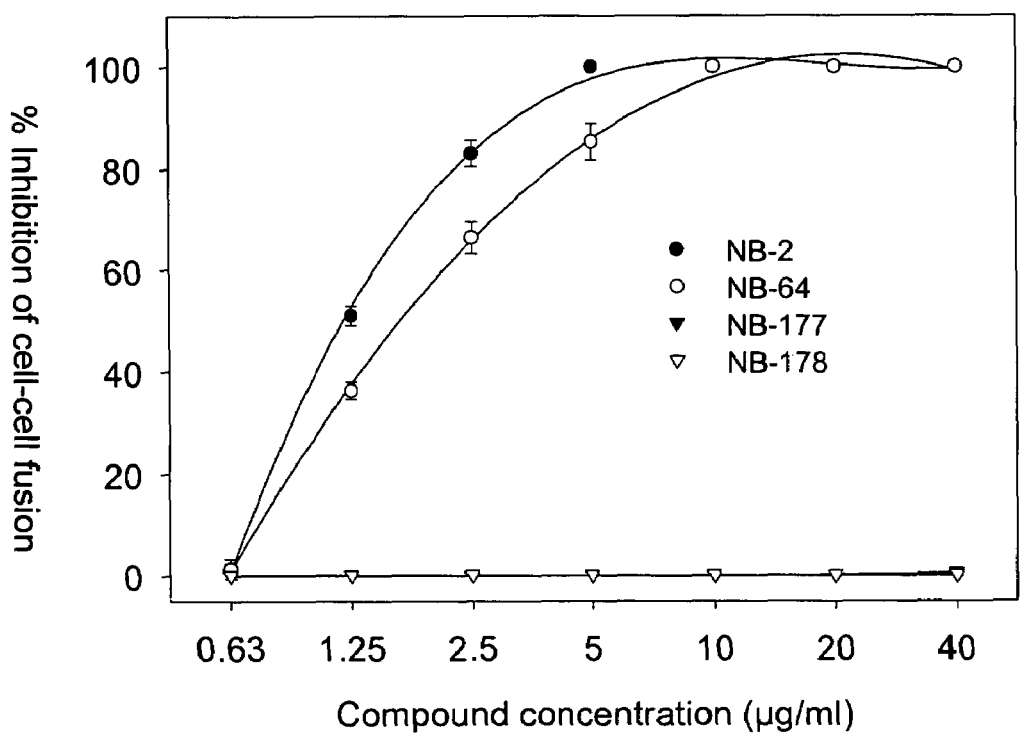

Figure 5
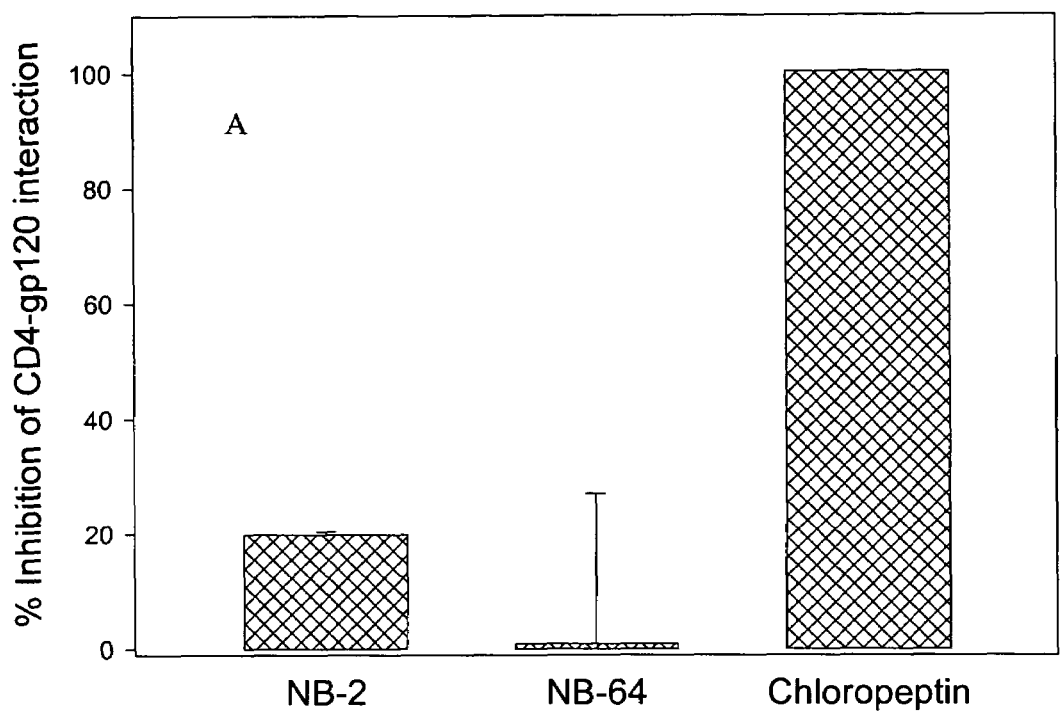
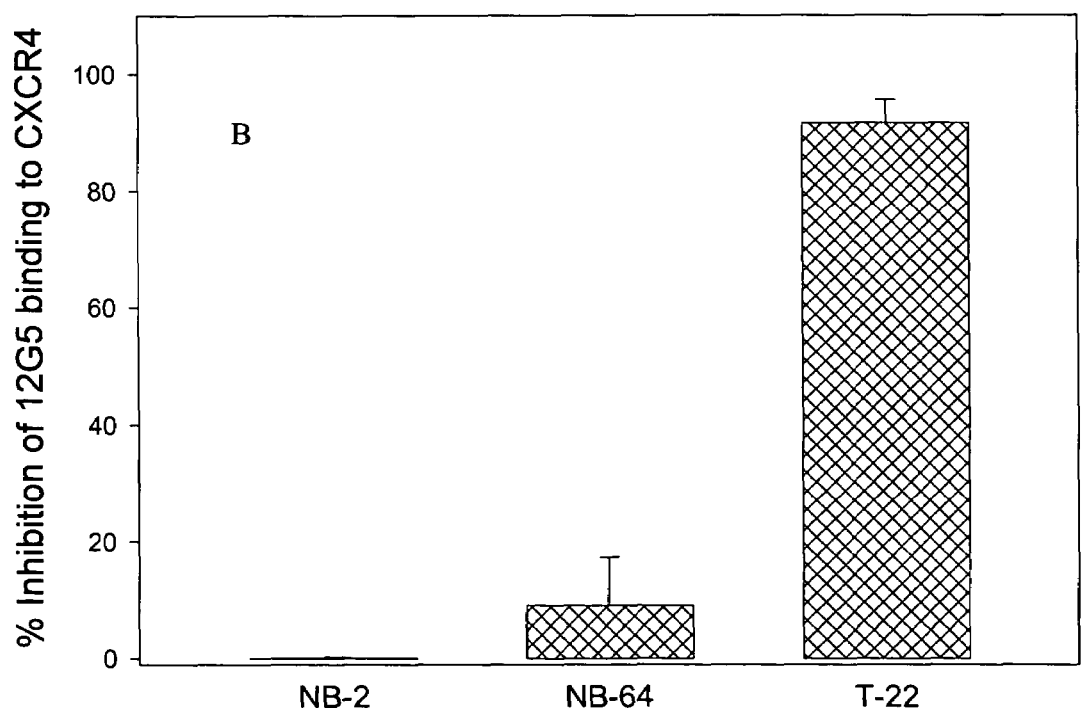

Figure 6
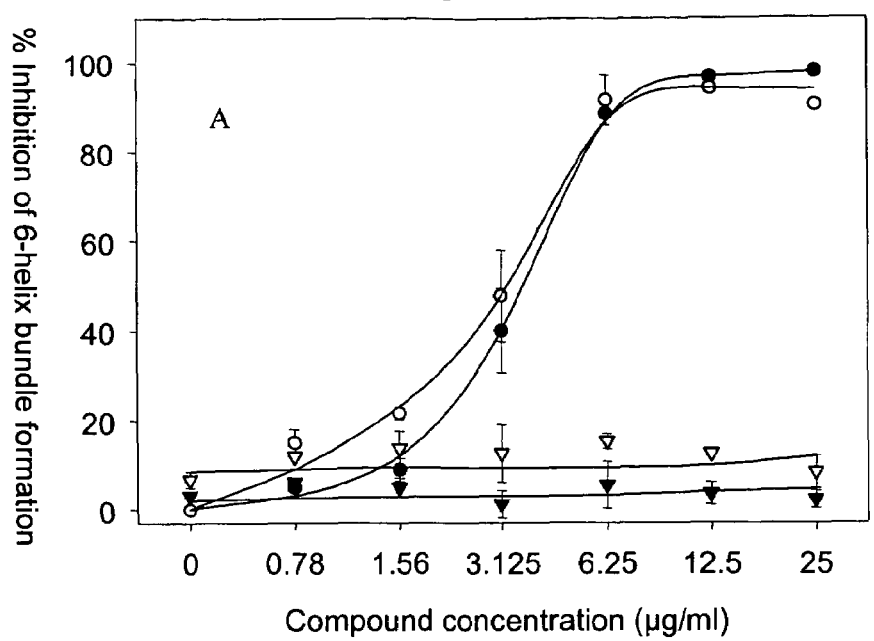
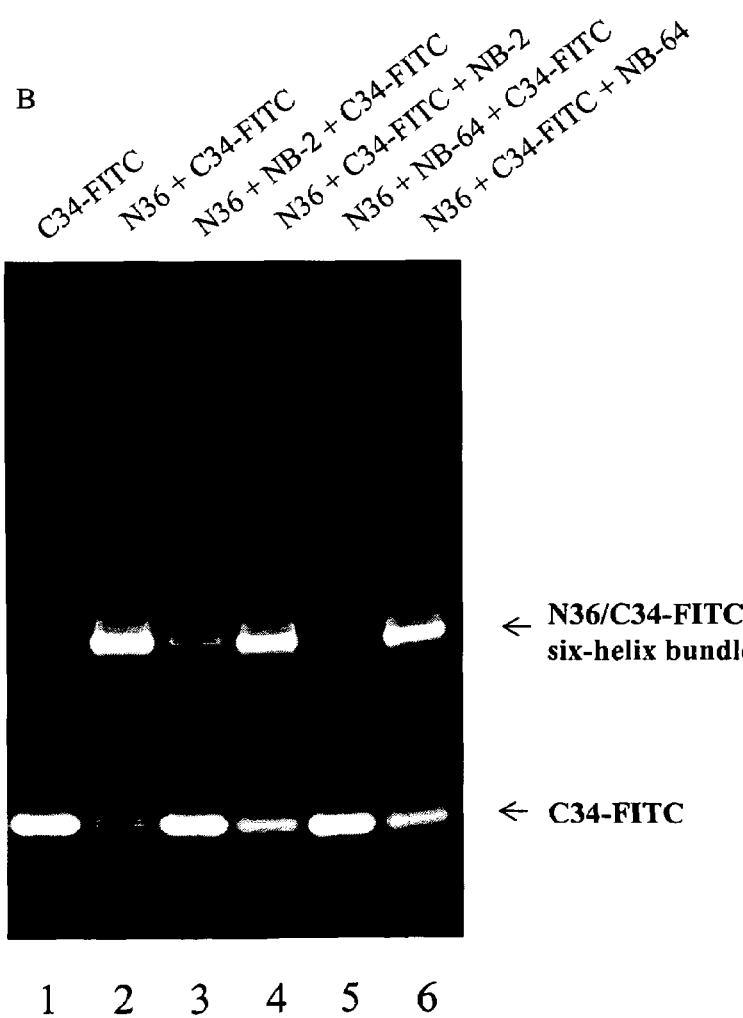

COMPOUNDS FOR INHIBITION OF HIV INFECTION BY BLOCKING HIV ENTRY

This application claims priority of U.S. Ser. No. 60/428,055, filed 21 Nov. 2002, the content of which is incorporated by reference hereinto this application.

The invention disclosed herein was supported in part by National Institute of Health Grant RO1 AI46221. Accordingly, the United States Government may have certain rights in this invention.

Throughout this application, various publications are referenced and full citations for these publications may be found in the text where they are referenced. Disclosures of these publications in their entireties are hereby incorporated by reference into this application to more fully describe the state of the art to which this invention pertains.

BACKGROUND OF THE INVENTION

Human immunodeficiency virus type 1 (HIV-1) envelope glycoprotein (Env) transmembrane subunit gp41 plays a crucial role in the early steps of viral entry into target cells (38) and may serve as an important target for development of HIV-1 entry inhibitors (4, 25). The gp41 molecule consists of three domains, i.e., cytoplasmic domain, transmembrane domain and extracellular domain (ectodomain). The ectodomain contains three major functional regions: the fusion peptide (FP), the N-terminal heptad repeat (NHR or HR1) and the C-terminal heptad repeat (CHR or HR2). Peptides derived from the NHR and CHR regions of gp41, designated N- and C-peptides, have potent antiviral activity against HIV-1 infection (21, 33, 49, 50). One of the C-peptides, T-20 (previously known as DP-178 and now as Fuzeon), has shown potent in vivo anti-HIV-1 activity in clinical trials for treatment of patients with HIV-1 infection and AIDS (27, 50) and was recently approved by the US FDA as the first member of a new class of anti-HIV drugs, known as HIV fusion inhibitors. Discovery of this drug is a great breakthrough in the development of anti-HIV drugs since it can be used for treatment of HIV-infected individuals who fail to respond to the currently available anti-retroviral drugs, such as HIV reverse transcriptase and protease inhibitors (26, 29). However, the future application of T-20 may be constrained due to its lack of oral availability and high cost of production. Therefore, it is essential to develop small molecule anti-HIV-1 compounds with a mechanism of action similar to that of C-peptides but without the disadvantages of the peptidic drugs.

In the study on the mechanism by which C-peptides inhibit HIV-1 fusion, it has been demonstrated that the gp41 N- and C-peptides mixed at equimolar concentrations form a stable α-helical trimer of antiparallel heterodimers, representing the fusion-active gp41 core (33, 35). Crystallographic analysis has revealed that this is a six-stranded α-helical bundle, in which three N-helices associate to form the central trimeric coiled-coil and three C-helices pack obliquely in an antiparallel manner into the highly conserved hydrophobic grooves on the surface of this coiled-coil (3, 46, 48). The C-helix interacts with the N-helix mainly through the hydrophobic residues in the grooves on the surface of the central coiled-coil trimer. Each of the grooves on the surface of the N-helix trimer has a deep hydrophobic pocket that accommodates three conserved hydrophobic residues in the gp41 CHR region (3), suggesting that this pocket is an attractive target for designing new class of anti-HIV-1 drugs, which may prevent the early fusion events (2, 3).

Using the gp41 pocket as the target structure, previously two small molecule compounds were identified, ADS-J1 (9, 19) and XTT formazan (51) by applying a computer-aided molecular docking techniques and a sandwich enzyme linked immunosorbent assay (ELISA) (23) using a monoclonal antibody (mAb), NC-1, which specifically recognizes the fusion-active gp41 core structure (20). These compounds inhibit HIV-1 fusion possibly by docking into the gp41 pocket and interfering with the formation of the gp41 six-helix bundle formation. However, they may not be good lead compounds for development of anti-HIV-1 drugs since both are dyes and contain several reactive groups. Nevertheless, the identification of these compounds is useful as a proof of concept that a small molecule organic compound might block the fusion-active gp41 six-helix bundle formation and inhibit HIV-1 entry. Here it is reported that the identification of two pyrrole derivatives, designated NB-2 and NB-64, as novel HIV-1 fusion inhibitors, which may interact with gp41 at the fusion-intermediate conformation, possibly binding to the gp41 hydrophobic pocket and surrounding area and block the gp41 six-helix bundle formation, thereby inhibiting the fusion between the viral and target cell membranes. NB-2 and NB-64 are "drug-like" compounds and may be used as leads for designing more potent HIV-1 entry inhibitors, which are expected to be developed as a new class of anti-HIV-1 drugs.

SUMMARY OF THE INVENTION

It is an object of the present invention to provide compounds, which are effective against HIV infection.

It is also an object of the present invention to provide compounds for design and development of a new class of anti-HIV drugs by blocking HIV entry.

It is a further object of the present invention to provide methods for inhibiting HIV replication or infectivity or treating HIV infection in a subject without inducing undesirable adverse effects.

The present invention comprises compounds of the formula I, or pharmaceutically acceptable salts thereof,

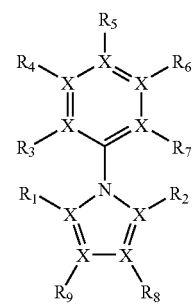

I

Wherein at least one of $R_1$, $R_2$, $R_3$, $R_4$, $R_5$, $R_6$, $R_7$, $R_8$, and $R_9$ contains COOH or other acidic groups.

In an embodiment, X can be C, N, O or S. When X is either O or S, the bond with the next atom such as C, will be a single bond and O or S will be unsubstituted. In a further embodiment, X is a carbon atom, wherein $R_1$ and $R_2$ are independently selected form the group consisting of H, alkyl, alkenyl, alkynyl, halogen, CN, nitro, OH and OR, where R is alkyl;

$R_3$, $R_4$, $R_5$, $R_6$, $R_7$, $R_8$, and $R_9$ are each independently selected from the group consisting of H, alkyl, cycloalkyl, alkenyl, alkynyl, aryl, arylalkyl, heterocyclyl, tetrazolyl, halogen, OH, CN, $NO_2$ and OR, where R is alkyl, COOR, where R is H and alkyl, $SO_3R$, where R is H and alkyl, $SO_2NHR$, where R is H and alkyl.

The group alkyl is represented by optionally substituted straight or branched alkyl chains carrying 1 to 6 carbon atoms and accordingly preferably stands for methyl, ethyl, n-propyl, i-propyl, n-butyl, i-butyl and tert-butyl.

The group alkenyl is represented by optionally substituted straight or branched alkenyl chains carrying 2 to 6 carbon atoms and accordingly preferably stands for vinyl, 1-propenyl, 2-propenyl, i-propenyl, and butenyl and its isomers.

The group alkynyl is represented by optionally substituted straight or branched alkynyl chains carrying 2 to 6 carbon atoms and accordingly preferably stands for ethynyl, propynyl and its isomers, butynyl and its isomers.

Suitable substituents of alkyl, alkenyl and alkynyl can be selected from one or more of amino, cyano, halogen, hydroxy, alkoxy, aryloxy, aryl, heterocyclyl, carboxy, nitro, alkyl sulfonyl, aryl sulfonyl, thio, alkyl thio, aryl thio.

The group cycloalkyl is represented by optionally substituted cycloalkyl groups containing 3 to 6 carbon atoms and can be selected, e.g., cyclopropyl, cyclobutyl, cyclopentyl, cyclohexyl, cycloheptyl or adamantyl. All these groups can also be benz-fused to an aromatic cyclic group, e.g., phenyl.

The group aryl is represented by optionally substituted phenyl or napthyl.

The group heterocyclic stands for optionally substituted saturated, partially saturated, aromatic cyclics, which contain one or more heteroatoms selected from nitrogen, oxygen and sulfur and can also be benz-fused to an optionally substituted aromatic cyclic or heterocyles.

Heterocyclic groups can be selected, but not limited to, from quinolinyl, pyridyl, indolyl, furyl, oxazolyl, thienyl, triazolyl, pyrazolyl, imidazolyl, benzothiazolyl, benzimidazolyl, piperzinyl, benzothiazolyl.

Substituents for aryl and heterocyclyl can be selected from those mentioned for alkyl.

The group halogen stands for chloro, bromo, fluoro and iodo.

Compounds of formula I, which are acidic in nature can form pharmaceutically acceptable salts with inorganic and organic bases, e.g., sodium hydroxide, potassium hydroxide, calcium hydroxide, barium hydroxide, magnesium hydroxide, N-ethyl piperidine, and similar other bases. When formula I is basic in nature it can form pharmaceutically acceptable salts with inorganic and organic acids, e.g., hydrochloric acid, sulfuric acid, nitric acid, phosphoric acid, acetic acid, tartaric acid, succinic acid, fumaric acid, maleic acid, malic acid, citric acid, methane sulfonic acid and similar others acids.

TABLE 1

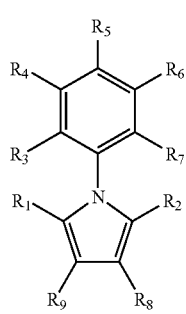

I

| Example # | Code # | $R_1$–$R_9$ |
|---|---|---|
| 1 | NB-1 | $R_1 = R_2 = CH_3$, $R_3 = R_4 = R_5 = H$, $R_6 = COOH$, $R_7 = CH_3$, $R_8 = R_9 = H$ |
| 2 | NB-2 | $R_1 = R_2 = CH_3$, $R_3 = H$, $R_4 = OH$, $R_5 = COOH$, $R_6 = R_7 = R_8 = R_9 = H$ |
| 3 | NB-4 | $R_1 = R_2 = CH_3$, $R_3 = R_4 = R_5 = H$, $R_6 = COOH$, $R_7 = R_8 = R_9 = H$ |

TABLE 1-continued

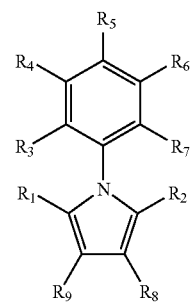

I

| Example # | Code # | $R_1$–$R_9$ |
|---|---|---|
| 4 | NB-26 | $R_1 = CH_3$, $R_2 = C_6H_5$, $R_3 = H$, $R_4 = COOH$, $R_5 = OH$, $R_6 = R_7 = R_8 = R_9 = H$ |
| 5 | NB-27 | $R_1 = CH_3$, $R_2 = C_6H_5$, $R_3 = H$, $R_4 = COOH$, $R_5 = Cl$, $R_6 = R_7 = R_8 = R_9 = H$ |
| 6 | NB-28 | $R_1 = CH_3$, $R_2 = C_6H_5$, $R_3 = H$, $R_4 = COOH$, $R_5 = R_6 = R_7 = R_8 = R_9 = H$ |
| 7 | NB-29 | $R_1 = R_2 = CH_3$, $R_3 = R_4 = H$, $R_5 = COOH$, $R_6 = Cl$, $R_7 = R_8 = R_9 = H$ |
| 8 | NB-50 | $R_1 = R_2 = CH_3$, $R_3 = R_4 = H$, $R_5 = COOCH_3$, $R_6 = R_7 = R_8 = R_9 = H$ |
| 9 | NB-53 | $R_1 = R_2 = CH_3$, $R_3 = R_4 = H$, $R_5 = COOH$, $R_6 = R_7 = R_8 = R_9 = H$ |
| 10 | NB-54 | $R_1 = R_2 = CH_3$, $R_3 = R_4 = H$, $R_5 = COOH$, $R_6 = Cl$, $R_7 = H$, $R_8 = CHO$, $R_9 = H$ |
| 11 | NB-56 | $R_1 = R_2 = CH_3$, $R_3 = H$, $R_4 = COOH$, $R_5 = OH$, $R_6 = R_7 = R_8 = R_9 = H$ |
| 12 | NB-63 | $R_1 = R_2 = R_3 = R_4 = R_5 = H$, $R_6 = COOH$, $R_7 = CH_3$, $R_8 = R_9 = H$ |
| 13 | NB-64 | $R_1 = R_2 = R_3 = H$, $R_4 = COOH$, $R_5 = Cl$, $R_6 = R_7 = R_8 = R_9 = H$ |
| 14 | NB-67 | $R_1 = R_2 = CH_3$, $R_3 = R_4 = H$, $R_5 = COOH$, $R_6 = H$, $R_7 = OH$, $R_8 = R_9 = H$ |
| 15 | NB-68 | $R_1 = R_2 = CH_3$, $R_3 = H$, $R_4 = COOH$, $R_5 = H$, $R_6 = COOH$, $R_7 = R_8 = R_9 = H$ |
| 16 | NB-69 | $R_1 = R_2 = CH_3$, $R_3 = H$, $R_4 = COOH$, $R_5 = R_6 = H$, $R_7 = OH$, $R_8 = R_9 = H$ |
| 17 | NB-70 | $R_1 = R_2 = CH_3$, $R_3 = R_4 = H$, $R_5 = Cl$, $R_6 = COOH$, $R_7 = R_8 = R_9 = H$ |
| 18 | NB-71 | $R_1 = R_2 = R_3 = CH_3$, $R_4 = R_5 = H$, $R_6 = COOH$, $R_7 = R_8 = R_9 = H$ |
| 19 | NB-72 | $R_1 = R_2 = CH_3$, $R_3 = R_4 = H$, $R_5 = COOH$, $R_6 = H$, $R_7 = CH_3$, $R_8 = R_9 = H$ |
| 20 | NB-97 | $R_1 = R_2 = R_3 = H$, $R_4 = COOH$, $R_5 = R_6 = R_7 = R_8 = R_9 = H$ |
| 21 | NB-99 | $R_1 = R_2 = CH_3$, $R_3 = R_4 = H$, $R_5 = COOH$, $R_6 = R_7 = H$, $R_8 = CHO$, $R_9 = H$ |

A synthetic peptide drug, T-20, has shown potent anti-HIV activity by blocking HIV entry in clinical trial. However, its future clinical application will be limited due to lack of oral availability. A group of organic compounds with low molecular weight having potent anti-HIV activity were identified by blocking HIV entry with a mechanism of action similar to that of T-20. Two representative compounds, designated NB-2 and NB-64, inhibited HIV replication (p24 production), HIV-mediated cytopathic effect (CPE) and cell fusion with low $IC_{50}$ values (Table 2). It was proved that NB-2 and NB-64 are HIV entry inhibitors by targeting the HIV gp41 since: 1) they inhibited HIV-mediated cell fusion; 2) they inhibited HIV replication only when they were added to the cells less than two hours after virus addition; 3)they did not block gp120-CD4 interaction; 4)they did not interact with the coreceptor CXCR4 since they failed to block anti-CXCR4 antibody binding to CXCR4-expressing cells; 5) they blocked the formation of the gp41 core detected by sandwich enzyme linked immunosorbent assay (ELISA)

using a conformation-specific MAb NC-1; 6) they inhibited the formation of the gp41 six-helix bundle revealed by fluorescence native-polyacrylamide gel electrophoresis (FN-PAGE); and 7) they blocked binding of D-peptide to the hydrophobic cavity within gp41 coiled coil domain, modeled by peptide IQN17. These results suggested that NB-2 and NB-64 may interact with the hydrophobic cavity and block the formation of the fusion-active gp41 coiled coil domain, resulting in inhibition of HIV-1 mediated membrane fusion and virus entry.

DETAILED DESCRIPTION OF THE FIGURES

For the purpose of illustrating the invention, there is shown in the drawings forms which are presently preferred. It is to be understood however, that the present invention is not limited to the precise arrangements and instrumentalities depicted in the drawings.

FIG. 1 Chemical structures of NB-2, NB-64, NB-177, and NB-178. Log P values were calculated using the ClogP software (Biobyte Corporation, Claremont, Calif.).

FIG. 2 NB-2 and NB-64 inhibited HIV-1 replication as indicated by suppression of p24 production. HIV-1$_{IIIB}$ was used in this assay. Each sample was tested in triplicate. Error bars indicate standard deviations.

Figure 3:
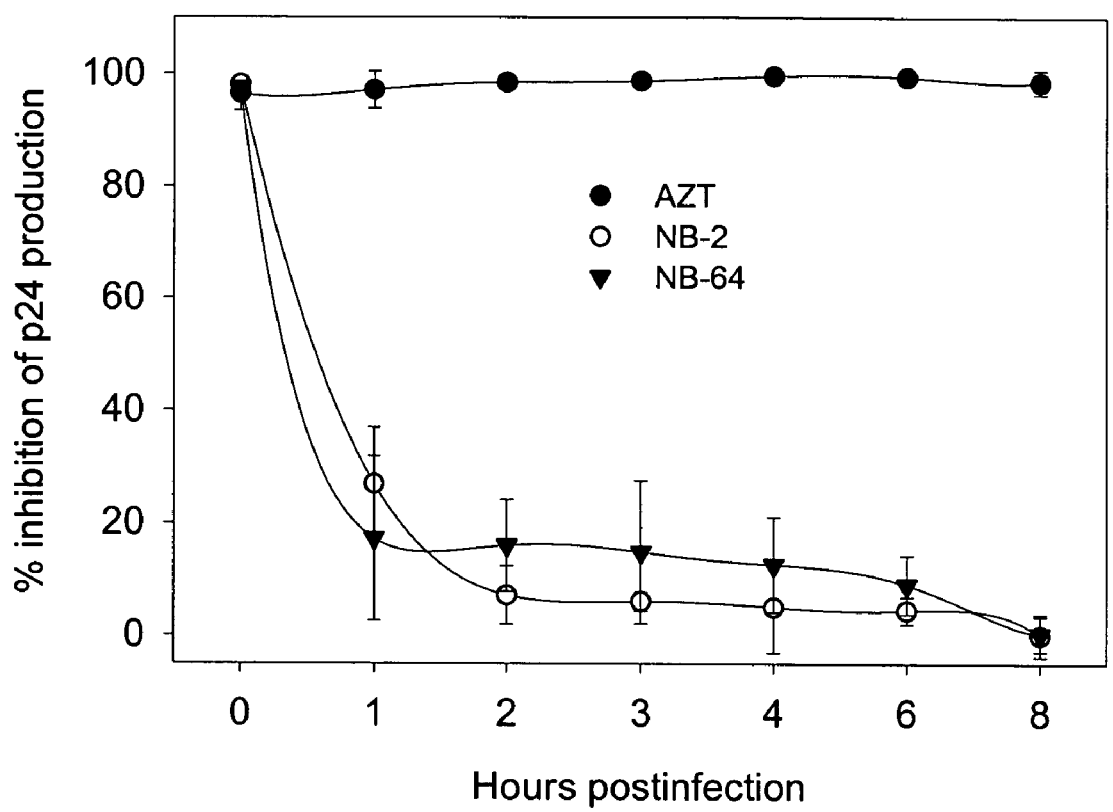

FIG. 3 NB-2 and NB-64 inhibited HIV-1 entry. Inhibition of HIV-1 entry was determined by a time-of-addition assay. NB-2 and NB-64 were added to MT-2 cells at different intervals post-infection by HIV-1$_{IIIB}$. AZT, a reverse transcriptase inhibitor, was included as a control. Each sample was tested in triplicate.

FIG. 4 NB-2 and NB-64 inhibited HIV-1 mediated membrane fusion. A) virus-cell fusion. Inhibition of fusion of HIV-1$_{NL4-3}$ pseudotyped viruses expressing envelope glycoprotein of the HIV-1$_{SF162}$ (R5) strain with U87-T4-CCR5 cells was determined by a luciferase assay. Each sample was tested in triplicate. B) Cell-cell fusion assay. Inhibition of fusion between HIV-1$_{IIIB}$ infected H9 cells (H9/HIV-1$_{IIIB}$) labeled with Calcein and MT-2 cells were assessed by a dye transfer assay as described in the Materials and Methods. Each sample was tested in quadruplicate.

FIG. 5 NB-2 and NB-64 did not block gp120-CD4 binding, nor interact with the coreceptor. A) Binding of gp120 to CD4 in the presence or absence of the compounds was assessed by ELISA. B) Binding of anti-CXCR4 antibody, 12G5, to CXCR4-expressing cells, U373-MAGI-CXCR4$_{CEM}$ cells, was determined by a cell-based ELISA (52). Each sample was tested in triplicate.

FIG. 6 NB-2 and NB-64 inhibited the gp41 six-helix bundle formation. A) Sandwich ELISA. The compounds NB-2 and NB-64 were incubated with N36 for 30 min at 37° C. before addition of C34. Samples were tested in triplicate. B) FN-PAGE. The peptide N36 was incubated with the NB-2 (lane 3) and NB-64 (lane 5) at 37° C. for 30 min before addition of the peptide C34-FITC, or with C34-FITC at 37° C. for 30 min before addition of the compounds NB-2 (lane 4) and NB-64 (lane 6), respectively. After incubation for another 30 min, the mixtures were analyzed by native PAGE as described in the Materials and Methods.

Figure 7:
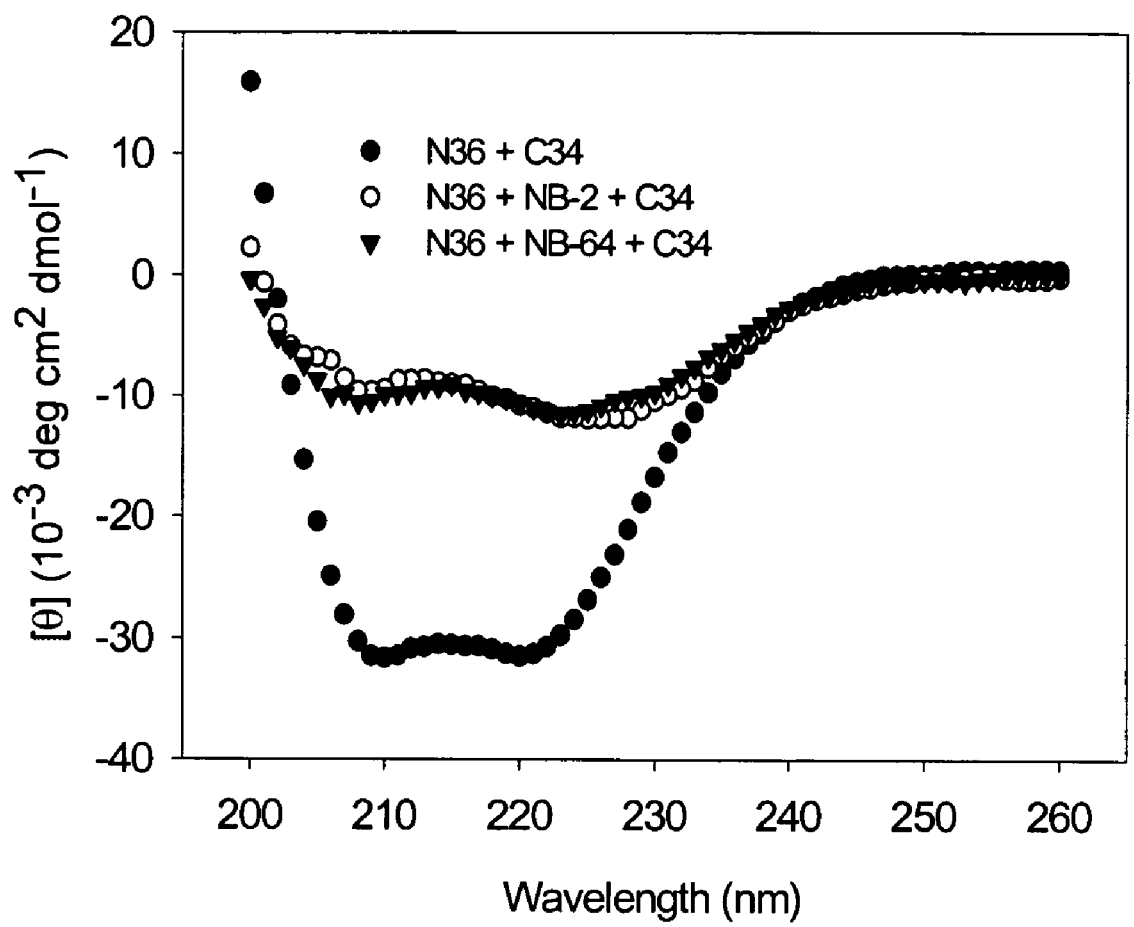

FIG. 7 NB-2 and NB-64 disrupted the a-helical conformation of the complex formed by N- and C-peptides by CD spectroscopy. Peptide N36 was incubated with NB-2 and NB-64 at 37° C. for 30 min before addition of C34. After incubation for additional 30 min, the mixture was measured by a CD spectrometer.

Figure 8:
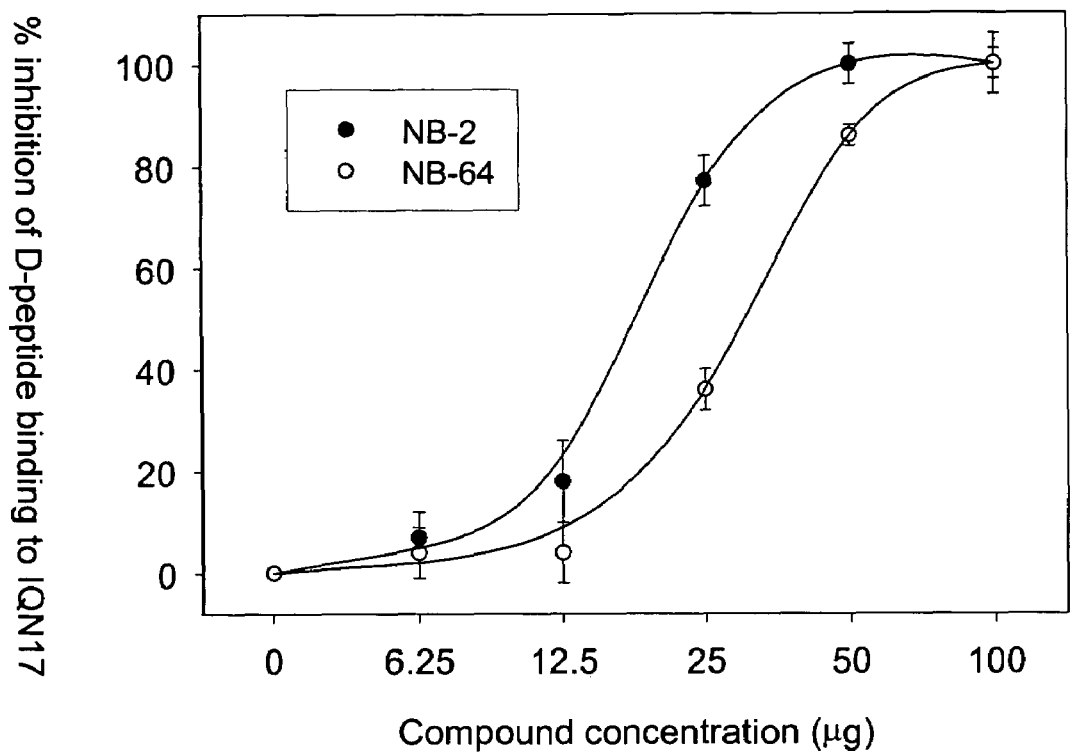

FIG. 8 NB-2 and NB-64 blocked a D-peptide binding to the gp41 pocket. The compounds NB-2 and NB-64, respectively, were incubated with biotinylated D10-p5-2k peptide at 37° C. for 30 min before addition of the peptide IQN17. Each sample was tested in triplicate.

DETAILED DESCRIPTION OF THE INVENTION

This invention provides compounds for inhibition of HIV infection. Specifically, this invention provides a compound of molecular weight from 200 to 1200 Daltons, and logP of −2.0 to +5.5, capable of interacting with the hydrophobic cavity and blocking the formulation of the fusion-active gp41 coiled core domain. In a preferred embodiment, the compound is negatively charged.

This invention also provides a method for screening compounds capable of blocking HIV entry. Screening methods of antiviral compounds targeted to the HIV-1 gp41 core structure were described in Patent Cooperation Treaty (PCT) application, PCT/US00/06771, publication no. WO 00/55377, U.S. Pat. No. 6,596,497. The content of this PCT application is hereby incorporated by reference into this application. For an example, antiviral compounds may be screened by the following method:

a) capturing polyclonal antibodies from an animal other than a mouse, directed against the HIV-1 gp41 trimeric structure containing three N-peptides of HIV-1 gp41 and three C-peptides of HIV-1 gp41, onto a solid-phase to form a polyclonal antibody coated solid-phase;

b) forming a mixture of a compound to be tested with N-peptides of HIV-1 gp41, and then adding C-peptides of HIV-1 gp41;

c) adding the mixture from step (b) to the polyclonal antibody coated solid-phase from step (a), then removing unbound peptides and unbound compound, and then adding a monoclonal antibody which specifically reacts with the HIV-1 gp41 and three C-peptides of HIV-1 gp41, but does not react with individual N-peptides of HIV-1 gp41 and does not react with individual C-peptides of HIV-1 gp41; and d) measuring the binding of said monoclonal antibody.

In a preferred embodiment, the monoclonal antibody used in screenings is designated NC-1. In another embodiment, the monoclonal antibody used is capable of competitively inhibiting bindings of the NC-1 antibody.

A biological assay may be used with the above immunoscreening assay. Said biological assay includes but is not limited to HIV-mediated cell fusion assay, as described infra.

The assay may also be fluorescence native polyacrylamide gel electrophoresis (FN-PAGE).

This invention also provides the compounds identified by the screenings. In accordance with the invention, a pharmaceutical composition for inhibition of HIV infection comprising the resulting compounds is provided.

As a result of the screening, this invention provides a compound having the following formula:

Wherein at least one of $R_1$, $R_2$, $R_3$, $R_4$, $R_5$, $R_6$, $R_7$, $R_8$, and $R_9$ contains COOH or other acidic groups.

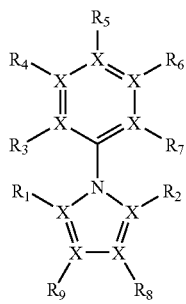

Wherein, X can be C or N. When N is at any X position, the corresponding R group may or may not be there. For example, if X is N at the $R_1$ site, then there will be no substitution if it is to maintain a double bond with the X at $R_9$ site. However, if X is N at the $R_1$ site but does not maintain a double bond with the X at $R_9$ site, it can then have $R_1$. In another embodiment, X is either O or S. When X is either O or S then the bond with the next atom, such as C, will be a single bond and O or S will be unsubstituted.

This invention provides a compound having formula I, wherein X is a carbon, or its pharmaceutically acceptable salts, Wherein:

$R_1$ and $R_2$ are independently selected from the group consisting of H, alkyl, alkenyl, alkynyl, halogen, CN, $NO_2$, OH and OR, where R is alkyl;

$R_3$, $R_4$, $R_5$, $R_6$, $R_7$, $R_8$, and $R_9$ are each independently selected from the group consisting of H, alkyl, cycloalkyl, alkenyl, alkynyl, aryl, arylalkyl, heterocyclyl, tetrazolyl, halogen, OH, CN, $NO_2$ and OR, where R is alkyl, NHR, where R is H and alkyl, COOR, where R is H, and alkyl, $SO_3R$, where R is H and alkyl, $SO_2NHR$, where R is H and alkyl.

In an embodiment, the group alkyl is substituted with straight or branched alkyl chains carrying 1 to 6 carbon atoms.

In another embodiment, alkyl is methyl, ethyl, n-propyl, i-propyl, n-butyl, i-butyl, or tert-butyl.

In a separate embodiment, alkenyl is substituted with straight or branched alkenyl chains carrying 2 to 6 carbon atoms. The alkenyl includes but is not limited to vinyl, 1-propenyl, 2-propenyl, i-propenyl, butenyl, or its isomers.

In an embodiment, alkynyl is substituted with straight or branched alkynyl chains carrying 2 to 6 carbon atoms. The alkynyl group includes but is not limited to ethynyl, propynyl or its isomers, or butynyl or its isomers.

In accordance with this invention, suitable substituents of alkyl, alkenyl and alkynyl can be selected from one or more of the following: amino, cyano, halogen, hydroxy, alkoxy, aryloxy, aryl, heterocyclyl, carboxy, nitro, alkyl sulfonyl, aryl sulfonyl, thio, alkyl thio, or aryl thio.

In an embodiment, this invention provides the above compound, wherein cycloalkyl is substituted with cycloalkyl groups containing 3 to 6 carbon atoms. The cycloalkyl includes but not limited to cyclopropyl, cyclobutyl, cyclopentyl, cyclohexyl, cycloheptyl and adamantyl. In a further embodiment, the cycloalkyl is benz-fused to an aromatic cyclic group.

In a separate embodiment, the aryl is substituted with phenyl or napthyl.

This invention provides the above compound, wherein the group heterocyclic is optionally substituted with saturated, partially saturated, or aromatic cyclics, which contain one or more heteroatoms selected from nitrogen, oxygen or sulfur. In an embodiment, the compound is benz-fused to a substituted aromatic cyclic or heterocyles. In a further embodiment, the heterocyclic group includes but is not limited to quinolinyl, pyridyl, indolyl, furyl, oxazolyl, thienyl, triazolyl, pyrazolyl, imidazolyl, benzothiazolyl, benzimidazolyl, piperzinyl, and benzothiazolyl.

This invention provides the above compound, wherein the halogen group is chloro, bromo, fluoro, or iodo.

This invention provides a compound having formula I, which is acidic and capable of forming pharmaceutically acceptable salts with inorganic and organic bases. The base includes but is not limited to sodium hydroxide, potassium hydroxide, calcium hydroxide, barium hydroxide, magnesium hydroxide, and N-ethyl piperidine.

This invention provides the compound having formula I, which is acidic and capable of forming pharmaceutically acceptable salts with inorganic and organic acids. The acid includes but is not limited to hydrochloric acid, sulfuric acid, nitric acid, phosphoric acid, acetic acid, tartaric acid, succinic acid, fumaric acid, maleic acid, malic acid, citric acid, and methane sulfonic acid.

This invention provides the above compound, wherein X is C; and $R_1$ and $R_2$ are $CH_3$, respectively; and $R_3$ is H; and $R_4$ is OH; and $R_5$ is COOH and $R_6$, $R_7$, $R_8$ and $R_9$ are each H.

This invention provides the above compound, wherein $R_1$, $R_2$ and $R_3$ are H, respectively; and $R_4$ is COOH, $R_5$ is Cl and $R_6$, $R_7$, $R_8$ and $R_9$ each are H and X is C.

This invention provides an antiviral pharmaceutical composition comprising an effective amount of a compound with formula I, or a pharmaceutically acceptable salt, and a pharmaceutically acceptable carrier.

A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules.

Typically such carriers contain excipients like starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

This invention provides the above pharmaceutical composition for treating human immunodeficiency virus (HIV) infection, further comprising an effective amount of an Acquired Immunodeficiency Syndrome (AIDS) treatment agent selected from the group consisting of anti-HIV agents, anti-infective agents, and immunomodulators.

This invention provides a method for inhibiting replication of human immunodeficiency virus in cells comprising of contacting cells with an effective amount of a compound with formula I to inhibit the replication of the human immunodeficiency virus.

This invention provides a method for treating mammals infected with the human immunodeficiency virus, comprising administering to said mammals an effective amount of a compound with formula I, or its pharmaceutically acceptable salts thereof.

In an embodiment, the mammal is a human.

This invention provides a method for preventing manifestation of Acquired Immunodeficiency Syndrome (AIDS) in a subject comprising administering to the subject an amount of a compound with formula I effective to prevent said syndrome in the subject.

The invention will be better understood by reference to the Examples which follow, but those skilled in the art will readily appreciate that the specific examples are only illustrative and are not meant to limit the invention as described herein, which is defined by the claims which follow thereafter.

EXPERIMENTAL DETAILS

Materials and Methods

Reagents. MT-2 cells, HIV-1$_{IIIB}$-infected H9 cells (H9/HIV-1$_{IIIB}$), U87-T4-CXCR4 and U87-T4-CCR5 cells, laboratory adapted and primary HIV-1 strains, and anti-p24 mAb (183-12H-5C) were obtained from the NIH AIDS Research and Reference Reagent Program. Lymphoid cell line CEMx174 5.25M7, kindly provided by C. Cheng-Mayer, is stably transduced with an HIV-1 long terminal repeat (LTR)-green fluorescent protein (GFP) reporter and lusiferase reporter construct. The cells express CD4 and both coreceptors, CXCR4 and CCR5 (16). These cells were maintained in RPMI-1640 medium supplemented with 10% FBS, 1 µg/ml puromycin, 200 µg/ml G418. Recombinant soluble CD4 (sCD4) was obtained from Genentech Inc. (South San Francisco, Calif.). Peptides N36, C34 (3, 35), IQN17 (11), and T22 (39, 40) were synthesized by a standard solid-phase FMOC method in the MicroChemistry Laboratory of the New York Blood Center. A biotinylated D-peptide, D10-p5-2K (11), was also synthesized in-house with D-amino acids and was oxidized as previously described (11). The peptides were purified to homogeneity by high-performance liquid chromatography (HPLC). The identity of the purified peptides was confirmed by laser desorption mass spectrometry (PerSeptive Biosystems). Rabbit antisera directed against the mixture of N36/C34 and against IQN17 were prepared as previously described (20). Mouse mAb NC-1 specific for the gp41 six-helix bundle was prepared and characterized as previously described (20). Rabbit and mouse IgG were purified using Protein A/G beads (Pierce, Rockford, Ill.). Mouse mAb 12G5 specific for CXCR4 was purchased from R&D Systems (Minneapolis, Minn.). Compounds used for screening were purchased from ChemBridge Corporation (San Diego, Calif.). NB-177 and NB-178 were purchased from Maybridge Plc (Trevillett, England). Chloropeptin was a generous gift from Satoshi Omura and Haruo Tanaka of The Kitasato Institute, Tokyo, Japan.

Syncytium-formation assay for screening HIV-1 fusion inhibitors. HIV-1$_{IIIB}$-infected H9 cells (H9/HIV-1$_{IIIB}$) at 2×10$^5$/ml were cocultured with MT-2 cells (2×10$^6$/ml) in the presence of compounds to be screened (final concentration of compound: 25 µg/ml) in a 96-well plate at 37° C. for 2 days. HIV-1 induced syncytium formation was observed under an inverted microscope and scored as "−" (no syncytium was observed), "±" (about 50% syncytia were inhibited), and "+" (no syncytium formation was inhibited). The compounds scored with "−" and "±" were selected for further screening by ELISA for inhibitors against the gp41 six-helix bundle formation.

ELISA for screening for compounds that inhibit the gp41 six-helix bundle formation. A sandwich ELISA as previously described (23) was used to screen for compounds that inhibit the gp41 six-helix bundle formation. Briefly, peptide N36 (2 µM) was pre-incubated with a test compound at the indicated concentrations at 37° C. for 30 min, followed by addition of C34 (2 µM). In the control experiments, N36 was pre-incubated with C34 at 37° C. for 30 min, followed by addition of the test compound. After incubation at 37° C. for 30 min, the mixture was added to wells of a 96-well polystyrene plate (Costar, Corning Inc., Corning, N.Y.) which were precoated with IgG (2 µg/ml) purified from rabbit antisera directed against the N36/C34 mixture. Then, the mAb NC-1, biotin-labeled goat-anti-mouse IgG (Sigma Chemical Co., St. Louis, Mo.), streptavidin-labeled horse-radish peroxidase (SA-HRP) (Zymed, S. San Francisco, Calif.), and the substrate 3,3',5,5'-tetramethylbenzidine (TMB) (Sigma) were added sequentially. Absorbance at 450 nm was measured using an ELISA reader (Ultra 384, Tecan, Research Triangle Park, N.C.). The percent inhibition by the compounds was calculated as previously described (18) and the concentration for 50% inhibition (IC$_{50}$) was calculated using the software designated Calcusyn (7), kindly provided by Dr. T. C. Chou (Sloan-Kettering Cancer Center, New York, N.Y.).

Assessment of anti-HIV-1 infectivity. The inhibitory activity of compounds on infection by laboratory-adapted HIV-1 strains was determined as previously described (18). In brief, 1×10$^4$ MT-2 cells were infected with HIV-1 at 100 TCID$_{50}$ (50% tissue culture infective dose) in 200 µl of RPMI 1640 medium containing 10% FBS in the presence or absence of compounds at graded concentrations overnight. For the time-of-addition assay, compounds were added at various time post-infection. Then the culture supernatants were removed and fresh media were added. On the fourth day post-infection, 100 µl of culture supernatants were collected from each well, mixed with equal volumes of 5% Triton X-100 and assayed for p24 antigen, which was quantitated by ELISA (51). Briefly, the wells of polystyrene plates (Immulon 1B, Dynex Technology, Chantilly, Va.) were coated with HIV immunoglobulin (HIVIG), which was prepared from plasma of HIV-seropositive donors with high neutralizing titers against HIV-1$_{IIIB}$ as previously described (44) in 0.085 M carbonate-bicarbonate buffer (pH 9.6) at 4° C. overnight, followed by washes with PBS-T buffer (0.01M PBS containing 0.05% Tween-20) and blocking with PBS containing 1% dry fat-free milk (Bio-Rad Inc., Hercules, Calif.). Virus lysates were added to the wells and incubated at 37° C. for 1 h. After extensive washes, anti-p24 mAb (183-12H-5C), biotin labeled anti-mouse IgG1 (Santa Cruz Biotech., Santa Cruz, Calif.), SA-HRP and TMB were added sequentially. Reactions were terminated by addition of 1N H$_2$SO$_4$. Absorbance at 450 nm was recorded in an ELISA reader (Ultra 384, Tecan). Recombinant protein p24 (US Biological, Swampscott, Mass.) was included for establishing standard dose response curve.

Inhibitory activity of compounds on infection by primary HIV-1 isolates was determined as previously described (41). PBMCs were isolated from the blood of healthy donors at the New York Blood Center by standard density gradient centrifugation using Histopaque-1077 (Sigma). The cells were plated in 75 cm$^2$ plastic flasks and incubated at 37° C. for 2 hrs. The nonadherent cells were collected and resuspended at 5×10$^6$ in 10 ml RPMI-1640 medium containing 10% FBS, 5 µg/ml PHA and 100 U/ml IL-2 (Sigma), followed by incubation at 37° C. for 3 days. The PHA-stimulated cells were infected with corresponding primary HIV-1 isolates at 0.01 multiplicity of infection (MOI) in the absence or presence of a compound at graded concentrations. Culture media were changed every 3 days. The supernatants were collected 7 days post-infection and tested for p24 antigen by ELISA as described above. The percent inhibition of p24 production and $IC_{50}$ values were calculated as described above.

Inhibition of cell-cell fusion. A dye transfer assay was used for detection of HIV-1 mediated cell fusion as previously described (21, 24, 34). H9/HIV-1$_{IIIB}$ cells were labeled with a fluorescent reagent, Calcein-AM (Molecular Probes, Inc., Eugene, Oreg.) and then incubated with MT-2 cells (ratio=1:5) in 96-well plates at 37° C. for 2 hrs in the presence or absence of compounds tested. The fused and unfused Cacein-labeled HIV-1-infected cells were counted under an inverted fluorescence microscope (Zeiss, Germany) with an eyepiece micrometer disc. The percentage of inhibition of cell fusion and the $IC_{50}$ values were calculated as previously described (21).

Inhibition of fusion between PBMCs infected by primary HIV-1 strains (X4 and R5 viruses) with CEMx174 5.25 M7 cells, which express CD4 and both coreceptors, CXCR4 and CCR5, was determined by a luciferase assay. Briefly, 50 µl of compound at graded concentration in triplicate was incubated with equal volume of PHA-stimulated PBMCs (1×10$^5$/ml) infected by corresponding primary HIV-1 strains, respectively, for 7 days as described above. After incubation at 37° C. for 30 min, 100 µl of CEMx174 5.25 M7 cells (2×10$^5$) were added and incubated at 37° C. for three days. The cells were collected, washed, and lysed with the lysing reagent included in the luciferase kit (Promega, Corp., Madison, Wis.). Aliquots of cell lysates were transferred to 96-well flat-bottom luminometer plates (Costar, Corning Inc., Corning, N.Y.), followed by addition of luciferase substrate (Promega). The luciferase activity was measured in the Ultra 384 luminometer (Tecan).

Inhibition of virus-cell fusion. Inhibition of fusion of HIV-1$_{NL4-3}$ pseudotyped viruses expressing envelope glycoprotein of the HIV-1$_{HXB2}$ (X4) and HIV-1$_{SF162}$ (R5) strains with U87-T4-CXCR4 and U87-T4-CCR5 cells, respectively, was measured as previously described (15). Briefly, 100 µl of U87-T4-CXCR4 and U87-T4-CCR5 cells, respectively, at 1×10$^5$ cells/ml were added to the wells of a 96-well tissue culture plate and cultured at 37° C. overnight. Fifty µl of a test compound at graded concentrations was mixed with 50 µl of the HIV-1$_{NL4-3}$-luc viruses pseudotyped with the HIV-1$_{HXB2}$ and HIV-1$_{SF162}$ Env, prepared as described previously (15), at a final p24 concentration of 0.5 ng/ml in the presence of Polybrene (10 µg/ml). After incubation at 37° C. for 30 min, the mixtures were added to the cells and incubated at 37° C. overnight. The supernatants were removed and fresh culture medium was added. After incubation at 37° C. for 3 days, the cells were washed twice with PBS and lysed with the lysing reagent included in a luciferase assay kit (Promega, Corp., Madison, Wis.). The cell lysates were transferred to a 96-well flat-bottom luminometer plate (Costar, Corning Inc., Corning, N.Y.) and luciferase substrate (Promega) was added. The luciferase activity was measured immediately on a luminometer (Ultra 384, Tecan). The % inhibition and $IC_{50}$ values were calculated as described above.

Detection of in vitro cytotoxicity. The in vitro cytotoxicity of compounds for MT-2 cells was measured using trypan blue dye exclusion assay (41). Briefly, 100 µl of MT-2 cells (2×10$^6$/ml) were incubated with an equal volume of a compound diluted in culture media at graded concentrations at 37° C. for 2 hr. Ten microliters of cell suspension was transferred to a well of round-bottom plate and mixed with 10 µl of 0.04% trypan blue solution. The number of viable cells was counted using a hemocytometer under a microscope. The $CC_{50}$ (the concentration for 50% cytotoxicity) values were calculated using the software Calcusyn (6).

Inhibition of gp120 binding to CD4. Wells of polystyrene plates was coated with 100 µl of sheep anti-gp120 antibody D7324 (Cliniqa, Fallbrook, Calif.) at 2 µg/ml in carbonate buffer (pH 9.6) at 4° C. overnight and blocked with 1% dry fat-free milk in PBS at 37° C. for 1 h. One hundred microliters of recombinant gp120 molecule (Immunodiagnostics, Woburn, Mass.) at 0.5 µg/ml in PBS was added and incubated at 37° C. for 1 h, followed by three washes with PBS-T. Soluble CD4 (sCD4) at 0.25 µg/ml was added in the presence of a compound (25 µM) and incubated at 37° C. for 1 h. After three washes, rabbit anti-sCD4 IgG (0.25 µg/ml in PBS, 100 µl/well) was added and incubated at 37° C. for 1 h. Binding of rabbit anti-sCD4 IgG was determined by sequential addition of biotinylated goat-anti-rabbit IgG, SA-HRP, and TMB. After the reactions were terminated, absorbance at 450 nm was recorded in an ELISA reader (Tecan).

Inhibition of anti-CXCR4 antibody binding to CXCR4-expressing cells. The inhibition of the binding of anti-CXCR4 antibody to CXCR4-expressing cells was determined using a cell-based ELISA as described previously (52). Briefly, U373-MAGI-CXCR4$_{CEM}$ cells (1×10$^5$/well) which express CXCR4 molecules were cultured in a 96-well plate at 37° C. overnight. The cells were fixed with 5% formaldehyde at room temperature for 15 min and washed with PBS-T. The cells were incubated with anti-CXCR4 mAb 12G5 at 37° C. for 1 h in the presence or absence of compounds tested. Isotype IgG2a was used as a control. After addition of biotin-labeled goat anti-mouse IgG, SA-HRP and the substrate TMB sequentially, the absorbance at 450 nm was measured using an ELISA reader (Tecan). The percentage of inhibition by the compounds was calculated as described above.

Circular dichroism (CD) spectroscopy. A test compound at graded concentrations was incubated with N36 in phosphate buffer (pH 7.2) at 37° C. for 30 min before addition of C34 in the same buffer at equimolar concentration. After incubation at 37° C. for 30 min, the mixture was cooled down and CD spectra of the mixture were measured on the J-715 CD spectrometer equipped with a thermoelectric temperature controller (Jasco, Japan). The instrument was calibrated using a two point calibration method with (+)-10-camphorsulfonic acid. The wavelength dependence of molar ellipticity (θ) was monitored at 0° C. by 5 scans in 1 nm increments with a sampling time of 10 seconds as previously described (12, 51). The CD signal at 222 nm was measured as a function of temperature. Thermal melts were performed in 2° C. steps, with 2 min of equilibration at each temperature and an acquisition time of 0.5 min. The midpoint of the thermal unfolding transition ($T_m$) was estimated from the maximum of the first derivative of the CD signal at 222 nm (1).

Fluorescence native polyacrylamide gel electrophoresis (FN-PAGE). FN-PAGE was performed as previously described (32). Briefly, 18% pre-cast Tris-Glycine gels and Novex X-Cell II Mini cell (Invitrogen, Carlsbad, Calif.) were used for native-PAGE. The peptide N36 (40 µM in PBS) was incubated with NB-2 and NB-64 at 200 µg/ml, respectively, at 37° C. for 30 min and the peptide C34-FITC (40 µM in PBS) was added. In the control, N36 was incubated with C34-FITC at 37° C. for 30 min before addition of the compounds. After incubation at 37° C. for another 30 min, the mixture was diluted in Tris-Glycine native sample buffer, then loaded to 10×1.0 mm wells. Gel electrophdrosis was carried out with 125 V constant voltage at room temperature for about 90 min in Tris-Glycine native running buffer. Immediately after electrophoresis, image of the fluorescence bands in the gel was taken by the FluorChem 8800 Imaging System (Alpha Innotech corp., San Leandro, Calif.) using a transillumination UV light source with excitation wavelength at 302 nm and a fluorescence filter with emission wavelength at 520 nm.

Inhibition of a biotinylated D-peptide binding to IQN17. For measuring the binding of a D-peptide, D10-p5-2k to IQN17, an ELISA was established. In brief, wells of a 96-well polystyrene plate were coated with IgG (10 μg/ml) purified from rabbit antisera directed against IQN17. The peptide IQN17 (10 μM) was incubated with a compound at graded concentrations at 37° C. for 30 min before addition of the peptide D10-p5-2K-biotin (5 μM). After incubation at 37° C. for 30 min, the mixture was added to the plate, followed by incubation at 37° C. for 30 min. After extensive washes, D10-p5-2K-biotin bound to the IQN17 was quantitated by addition of SA-HRP and TMB sequentially. The absorbance at 450 nm was read using an ELISA reader (Tecan). The percentage of inhibition by the compounds was calculated as described above.

Results

Identification of Two Anti-HIV-1 Compounds, NB-2 and NB-64, Through HTS

Using syncytium formation assay and sandwich ELISA-based HTS techniques, a chemical library from ChemBridge Corporation consisting of 33,040 compounds at a single dose (25 μg/ml) has been screened. These compounds are "drug-like" molecules which were rationally pre-selected to form a "universal" library that covers the maximum pharmacophore diversity with the minimum number of compounds. Two compounds, termed NB-2 and NB-64, at this concentration are found to have significantly inhibited HIV-1 mediated syncytium formation and the six-helix bundle formation between the gp41 N-peptide N36 and C-peptide C34. Both NB-2 and NB-64 are N-substituted pyrrole derivatives with the molecular weights of 231 and 222 daltons, and ClogP (a measure of partition of a drug in water and octanol phase) of 4.15 and 3.15, respectively (FIG. 1). Another two N-substituted pyrrole derivatives, NB-177 and NB-178, were obtained from Maybridge as controls. These two compounds have the same parent structure as NB-2 and NB-64, respectively, except that they do not have the COOH group (FIG. 1). But NB-177 and NB-178 had no inhibitory activity in above two screening assays.

NB-2 and NB-64 have Potent Inhibitory Activity on Infection by Laboratory-adapted and Primary HIV-1 Strains The inhibitory activity of NB-2 and NB-64 on infection of MT-2 cells by laboratory-adapted HIV-1 strains and of PBMCs by primary HIV-1 strains was determined as previously described (18, 41). The in vitro cytotoxicity of NB-2 and NB-64 were determined using trypan blue exclusion assay (51).

As shown in FIG. 2, both NB-2 and NB-64 significantly inhibited HIV-1$_{IIIB}$ replication, while NB-177 and NB-178, have no inhibitory activity at the concentration up to 80 μg/ml. Both NB-2 and NB-64 had low in vitro cytotoxicity and high selectivity index (SI>1,000) (Table 2), suggesting NB-2 and NB-64 are potent anti-HIV-1 agents. In addition to HIV-1$_{IIIB}$, NB-2 and NB-64 also inhibited other laboratory-adapted HIV-1 strains, including one strain resistant to AZT (AZT-R) Both compounds had potent inhibitory activity on infection by primary HIV-1 strains with distinct genotypes and biotypes, although some primary HIV-1 strains (e.g., RU570) were less sensitive than other strains. These results suggest that NB-2 and NB-64 have potent antiviral activity against a broad spectrum of HIV-1 strains.

TABLE 2

The in vitro cytotoxicity of NB-2 and NB-64 and their inhibitory activity on HIV-1$_{IIIB}$ replication

| Compounds | NB-2 | NB-64 |
|---|---|---|
| $CC_{50}$ (μg/ml) | 305.60 ± 5.04 | >500 |
| $IC_{50}$ (μg/ml) | 0.24 ± 0.05 | 0.49 ± 0.09 |
| SI ($CC_{50}/IC_{50}$) | 1271 | >1020 |

TABLE 3

Inhibitory activity of NB-2 and NB-64 on infection by laboratory-adapted and primary HIV-1 strains

| | $IC_{50}$ (μg/ml) for inhibition of p24 production | |
|---|---|---|
| HIV-1 strain | NB-2 | NB-64 |
| Laboratory-adapted | | |
| RF (clade B, X4) | 0.45 ± 0.04 | 0.96 ± 0.03 |
| SF2 (clade B, X4) | 0.44 ± 0.03 | 1.34 ± 0.06 |
| AZT-R (clade B, X4) | 1.41 ± 0.03 | 6.25 ± 0.25 |
| Primary | | |
| 94UG103 (clade A, X4R5) | 5.92 ± 0.06 | 7.94 ± 0.96 |
| 92US657 (clade B, R5) | 10.41 ± 1.88 | 6.60 ± 1.80 |
| 93IN101 (clade C, R5) | 1.05 ± 0.23 | 4.38 ± 0.19 |
| 93TH051 (clade E, X4R5) | 1.15 ± 0.14 | 5.24 ± 1.80 |
| 93BR020 (clade F, X4R5) | 2.50 ± 0.01 | 1.05 ± 0.18 |
| RU570 (clade G, R5) | 23.12 ± 1.23 | 8.81 ± 0.24 |
| BCF02 (Group O, R5) | 0.21 ± 0.12 | 1.31 ± 0.90 |

TABLE 4

Inhibitory activity of NB-2 and NB-64 on HIV-1 mediated cell-cell fusion

| | $IC_{50}$ (μg/ml) for inhibition of cell-cell fusion | |
|---|---|---|
| Fusion between | NB-2 | NB-64 |
| MT-2 & H9/HIV-1$_{IIIB}$ | | |
| (clade B, X4) | 1.53 ± 0.17 | 2.02 ± 0.19 |
| 5.25M7 & PBMCs/SF162 | | |
| (clade B, R5) | 4.86 ± 0.34 | 20.86 ± 0.20 |
| 5.25M7 & PBMCs infected by | | |
| 92UG029 (clade A, X4) | 2.50 ± 0.02 | 2.21 ± 0.56 |
| 92UG657 (clade B, R5) | 6.64 ± 1.13 | 39.00 ± 5.27 |
| 93IN101 (clade C, R5) | 3.27 ± 0.18 | 18.26 ± 0.01 |
| 93UG065 (clade D, X4R5) | 6.07 ± 0.07 | 20.77 ± 1.94 |
| CMU02 (clade E, R5) | 8.14 ± 1.09 | 4.89 ± 1.08 |
| 93TH051 (clade E, X4R5) | 1.76 ± 0.07 | 12.72 ± 0.32 |
| 93BR020 (clade F, X4R5) | 1.66 ± 0.07 | 2.24 ± 0.31 |
| BCF02 (Group O, R5) | 0.93 ± 0.57 | 10.30 ± 5.90 |

NB-2 and ND-64 Inhibit HIV-1 Entry by Blocking Membrane Fusion

A time-of-addition assay was carried out to determine whether NB-2 and NB-64. are HIV-1 entry inhibitors. MT-2 cells were incubated with HIV-1$_{IIIB}$ at 37° C. for 0, 1, 2, 3, 4, 6, and 8 hrs, respectively, before addition of the test compounds at 10 μg/ml. AZT (2.5 μM) was used as a control. After culture for another 2 hrs, the cells were washed to remove the free virus and compounds. The supernatants were collected on day 4 post-infection for measurement of p24 production. NB-2 and NB-64 inhibited HIV-1 replication when they were added to the cells with virus together, but showed no inhibitory activity if they were added one hour or longer after virus was added to cells. However, AZT was still effective in inhibiting HIV-1 replication even it was added 8 hrs post-infection (FIG. 3).

Fusion between virus and target cell membranes or between HIV-infected cells and uninfected cells is the critical steps of HIV entry into a new target cell. Therefore, it is essential to determine whether NB-2 and NB-64 inhibit virus-cell and cell-cell fusion. As shown in FIG. 4A, both NB-2 and NB-64 inhibited fusion of HIV-1$_{NL4-3}$ pseudotyped viruses expressing HIV-1$_{SF162}$ (R5) Evn with U87-T4-CCR5 (IC$_{50}$ values=3.35±0.32 and 2.79±0.57 pg/ml, respectively), while NB-177 and NB-178 had no inhibitory activity (FIG. 4B). A similar result was obtained by using the pseudotyped viruses expressing HIV-1$_{HXB2}$ (X4) Env and U87-T4-CXCR4 cells (data not shown). NB-2 and NB-64 also significantly inhibited fusion of HIV-1$_{IIIB}$ infected H9 cells with uninfected MT-2 cells with IC$_{50}$ values of 1.53±0.17 and 2.02±0.19 μg/ml, respectively. However, NB-177 and NB178 had no inhibitory activity on cell-cell fusion (FIG. 4B). Furthermore, NB-2 and NB-64 inhibited fusion between CEMx174 5.25M7 cells and PBMCs infected by primary HIV-1 strains with distinct genotypes and phenotypes (Table 4). These results suggest that NB-2 and NB-64 inhibit HIV-1 entry by blocking HIV-1 mediated membrane fusion.

NB-2 and NB-64 do not Block gp120-CD4 Binding, nor Interact with the Coreceptor CXCR4

The process of HIV-1 entry into a CD4$^+$ target cell can be divided into three steps: 1) the virus Env surface subunit gp120 binds to the CD4 molecule; 2) the gp120-CD4 complex interacts with a coreceptor (CXCR4 or CCR5) on target cells; and 3) the transmembrane subunit gp41 changes conformation to form the fusion-active six-helix bundle, resulting in the fusion of viral envelope with the target cell membranes (45). In the following experiments, which step of the HIV-1 entry is blocked by NB-2 and NB-64 was investigated.

First, it was determined whether NB-2 and NB-64 block CD4-gp120 interaction. HIV-1 envelope glycoprotein gp120 was captured by the anti-gp120 antibody coated onto wells of polystyrene plates. Soluble CD4 (sCD4) was added in the presence or absence of NB-2 and NB-64. Chloropeptin, a gp120-CD4 binding inhibitor having a potent anti-HIV-1 activity (36), was used as a control. After extensive washes, CD4 molecule bound to gp120 was quantitated by ELISA using anti-CD4 antibody. The results indicated that chloropeptin at 10 μg/ml markedly inhibited gp120-CD4 binding, while NB-2 and NB-64 at the same concentration did not significantly inhibited the interaction between CD4 and gp120 (FIG. 5A), suggesting that NB-2 and NB-64 are not targeted to the gp120-CD4 binding step.

Then, it was determined whether NB-2 and NB-64 bind to the HIV-1 coreceptor CXCR4 by a cell-based ELISA as previously described (52) using a mAb 12G5, which specifically recognizes CXCR4 and blocks HIV-1 infection of CXCR4$^+$ cells (37). T22, a CXCR4 inhibitory peptide (39), was used as a control. As shown in FIG. 5B, T22 at 25 μM significantly inhibited 12G5 binding to U373-MAGI-CXCR4$_{CEM}$ cells, a CXCR4-expressing cell line. However, at the same concentration, NB-2 and NB-64 had no inhibitory activity in this assay, suggesting that NB-2 and NB-64 do not interact with the HIV-1 coreceptor CXCR4 (FIG. 5B).

NB-2 and NB-64 Interfere with the gp41 Six-Helix Bundle Formation

Subsequently, a determination was made as the effect of NB-2 and NB-64 on the gp41 six-helix bundle formation, a critical conformational change during HIV-1 fusion with the target cells. A model system of the gp41 six-helix bundle was established by mixing the N- and C-peptides at equal molar concentrations (33). This model gp41 core structure can be detected by sandwich ELISA using a conformation-specific mAb, NC-1 (20, 23). Using this system, the inhibitory activity of NB-2 and NB-64 on the gp41 six-helix bundle formation was tested. As shown in FIG. 6A, NB-2 and NB-64 significantly inhibited the six-helix bundle formation between N36 and C34 in a dose-dependent manner. Their analogs, NB-177 and NB-178 had no inhibitory activity on the six-helix bundle formation at the concentrations up to 80 μg/ml (data not shown). These results suggest that NB-2 and NB-64 may bind to a component in the gp41 coiled coil domains and interfere with the association between the gp41 NHR and CHR regions.

A convenient biophysical method, FN-PAGE, was previously developed for revealing the visible bands of gp41 core formed by N36 and FITC-conjugated C34 (C34-FITC) (32). This method was used to detect the inhibitory activity of NB-2 and NB-64 on the gp41 core formation. As shown in FIG. 6B, in the absence of N36, C34-FITC showed a clear band at the lower position (lane 1). When N36 and C34-FITC was mixed together, two bands were revealed (lane 2). The major band at the upper position corresponds to the gp41 six-helix bundle formed by N36 and C34-FITC as confirmed by Western blot using the mAb NC-1 (32). The minor band at the lower position is the isolated C34-FITC. When the compounds NB-2 (lane 3) and NB-64 (lane 5) were preincubated with N36 before addition of C34-FITC, the intensity of the upper bands were significantly decreased while that of the lower bands were increased, suggesting that the gp41 six-helix bundle formation between N36 and C34 were inhibited by these two compounds and more isolated C34-FITC was accumulated. However, if N36 was preincubated with C34-FITC before addition of NB-2 (lane 4) and NB-64 (lane 6), the six-helix bundle formation was not inhibited, indicating that NB-2 and NB-64 may interact with a component in the gp41 NHR region, thus blocking the formation of the fusion-active gp41 core. However, once the six-helix bundle is formed, these two compounds cannot disrupt it.

NB-2 and NB-64 Interfere with the Conformational Change during the Interaction Between N- and C-peptides Previous studies demonstrated that the isolated N-peptide had tendency to aggregate and C-peptide had a random coil structure in aqueous solution. However, the mixture of the N- and C-peptides shows a typical α-helical conformation, as measured by CD spectroscopy (33), suggesting that the interaction between N- and C-peptides results in the change of their secondary structure to an α-helical coiled-coil conformation. Using a CD spectrophotometer (Model J-715, Jasco Inc., Japan), it is demonstrated that NB-2 and NB-64 at 100 μg/ml significantly disrupted the α-helicity of the N36/C34 mixture (FIG. 7). These results confirm that these two compounds interfere with the conformational change during the interaction between the N- and C-peptides.

NB-2 and NB-64 Blocked Binding of a D-peptide to the Pocket Presented on the gp41 Trimer Modeled by IQN17

During the process of HIV-1 fusion with the target cell membrane, the gp41 NHR and CHR regions associate to form fusogenic core structure. There are three highly conserved symmetrical hydrophobic grooves on the surface of the internal trimeric coiled-coil (3, 46, 48) and each of the grooves contains a deep hydrophobic pocket, which is an attractive target for HIV-1 entry inhibitors (2, 3). Eckert et al. identified a short circular anti-HIV-1 peptide consisting of D-amino acids, designated D10-p5-2K. This peptide specifically binds to the pocket presented on the IQN17, which mimics the gp41 central trimeric coiled-coil domain. Similar approach was used to determine whether NB-2 and NB-64 bind to the pocket and block D10-p5-2K binding to the pocket on IQN17 trimer. As shown in FIG. 8, both NB-2 and NB-64 significantly inhibited biotinylated D10-p5-2K binding to IQN17. These results suggest that NB-2 and NB-64 may interact with the hydrophobic pocket in the gp41 central trimer and block the interaction between the viral gp41 NHR and CHR regions to form the six-helix bundle, resulting in inhibition of HIV-1 entry and replication.

Discussion

During the past 20 years, one of the greatest progresses in HIV/AIDS research is the development of anti-HIV drugs (13). So far, 20 anti-HIV drugs have been approved by the US FDA and more drug candidates are in the pipelines (13, 43). Most of these drugs are targeted to the HIV-1 reverse transcriptase and protease. Only one of them, Fuzeon (T-20) targets the viral envelope glycoprotein gp41 (5, 17, 29, 50). T-20 (50), like other peptides derived from the HIV-1 gp41 CHR region, such as SJ-2176 (21, 22) and C34 (35), inhibits HIV-1 fusion and entry. It has shown great promise against HIV replication in clinical trials (28, 29). However, it has two major limitations: lack of oral availability (delivered by subcutaneous injection) and high cost of production (43). Thus, development of small molecule HIV-1 fusion inhibitors is urgently needed.

It was previously reported that the identification of a small molecule HIV-1 fusion inhibitor, ADS-J1, through screening using computer-aided molecular docking techniques and a sandwich ELISA using a conformation-specific mAb NC-1 (9, 23). However, this compound is not a good lead compound since it is a dye with azo bonds and several reactive groups. In addition, it has a molecular size of 1,087 daltons, larger than most "drug-like" compounds. Therefore, it was necessary to screen chemical libraries consisting of "drug-like" compounds using a syncytium formation assay for the primary screening and the ELISA for the secondary screening. Although the ELISA is convenient for high throughput screening of HIV-1 fusion inhibitors targeting gp41 (23), it may miss the anti-HIV-1 compounds that are targeted to other steps of HIV-1 entry, such as gp120 binding to CD4 and the coreceptors (CXCR4 or CCR5). Therefore, a syncytium formation assay for the primary screening was used since this assay can pick up the HIV-1 fusion inhibitors targeting to any step of HIV-1 entry.

Using this two-step screening assays, it was identified that two HIV-1 fusion inhibitors, NB-2 and NB-64, from a chemical library consisting of 33,040 "drug-like" compounds. These two compounds have the same parent structure and are N-substituted pyrrole derivatives. Both are water soluble and "drug-like" compounds based on the Lipinski's "rule of five" (31), i.e., molecular weight<500 daltons, the calculated CLogP<5, H-bond donors<5 and H-bond acceptors<10. Therefore, these two compounds may have good permeability and bioavailability.

NB-2 and NB-64 have potent anti-HIV-1 activity and low cytotoxicity. They inhibited HIV-1$_{IIIB}$ replication at concentration<0.5 µg/ml and selectivity index (SI)>1,000. The compounds have broad specificity against infection by both laboratory-adapted and primary HIV-1 strains with distinct genotypes and phenotypes. The evidence shows that NB-2 and NB-64 interferes with the HIV-1 entry step, more specifically, the process of gp41-mediated fusion between viral and target cell membranes as confirmed by a time-of-addition assay (FIG. 3) and virus-cell and cell-cell fusion assays (FIG. 4). The process of HIV-1 entry into target cell can be divided into three steps, i.e., gp120-CD4 interaction, gp120-CD4 complex binding to a coreceptor (CXCR4 or CCR5) and gp41 conformational changes. Here it has been demonstrated that NB-2 and NB-64 cannot block the interaction between gp120 and CD4 molecules (FIG. 5A), nor interact with CXCR4 (FIG. 5B). However, they do interfere with the gp41 conformational changes by blocking the formation of the fusion-active gp41 six-helix bundles as demonstrated by several assay systems (FIGS. 6 and 7).

Although design of small molecule organic compounds to block protein-protein interaction is a challenging approach for drug development (8), identification of such inhibitors have been reported (14, 42, 47). Most recently, a small molecule HIV-1 entry inhibitor, BMS-378806, was discovered (30). This compound with a molecular weight of 406.5 is very potent to block interaction between the viral envelope glycoprotein gp120 and the cellular receptor CD4. This suggests that a small molecule compound, if binds to a "hot spot" in a protein, such as a pocket, may effectively block protein-protein interaction. The deep hydrophobic pocket in the groove on the surface of the gp41 internal trimer formed by the NHR domains has been recognized as a "hot spot" since it may play important roles in the formation and the stability of the gp41 six-helix bundle (2, 10). NB-2 and NB-64 may bind to the gp41 pocket since it blocks the binding of D10-p5-2k peptide to the pocket in the grooves formed by IQN17, a hybrid molecule of GCN4 peptide and the pocket-containing N-peptide portion (FIG. 8).

To determine the role of the acidic group in NB-2 and NB-64, Two N-substituted pyrrole derivatives, NB-177 and NB-178 have been tested, which have the same parent structure as NB-2 and NB-64, respectively, except that they do not have the COOH group (FIG. 1). These compounds had no inhibitory activity on HIV-1 replication (FIG. 2), HIV-1 mediated virus-cell and cell-cell fusion (FIG. 4), and the gp41 six-helix bundle formation (FIG. 6), suggesting that the acid group in the NB-2 and NB-64 is critical for their antiviral activity, consistent with our previous observation on ADS-J1 which has several acid groups and one of them forms a salt bridge with the positively charged residue, lysine 574 (K574) in the gp41 NHR pocket-forming region (19). These results suggest that NB-2 and NB-64 may interact with a "hot spot" in the gp41 N-helix coiled coil domain through hydrophobic and ionic interactions and block the formation of the fusion-active gp41 core, resulting in inhibition of HIV-1 mediated membrane fusion and virus entry.

NB-2 and NB-64 have broad anti-HIV-1 activity against distinct primary HIV-1 strains and specificity to target gp41. Thus, NB-2 and NB-64 may be used as leads for designing more potent small molecule HIV-1 entry inhibitors as a new class of anti-HIV-1 drugs.

REFERENCES

1. Cantor, C. and P. Schimmerl. 1980. Biophysical Chemistry, Part III, p. 1131-1132. W.H. Freeman and Company, New York.
2. Chan, D. C., C. T. Chutkowski, and P. S. Kim. 1998. Evidence that a prominent cavity in the coiled coil of HIV type 1 gp41 is an attractive drug target. Proc. Natl. Acad. Sci. USA 95:15613-15617.
3. Chan, D. C., D. Fass, J. M. Berger, and P. S. Kim. 1997. Core structure of gp41 from the HIV envelope glycoprotein. Cell 89:263-273.
4. Chan, D. C. and P. S. Kim. 1998. HIV entry and its inhibition. Cell 93:681-684.
5. Chen, C. H., T. J. Matthews, C. B. McDanal, D. P. Bolognesi, and M. L. Greenberg. 1995. A molecular clasp in the human immunodeficiency virus (HIV) type 1 TM protein determines the anti-HIV activity of gp41 derivatives: implication for viral fusion. J. Virol. 69: 3771-3777.
6. Chou, T. C. and P. Talalay. 1984. Quantitative analysis of dose-effect relationships: the combined effects of multiple drugs or enzyme inhibitors. Adv. Enzyme Regul. 22:27-55.
7. Chou, T. -C. and Hayball, M. P. CalcuSyn: Windows Software for Dose Effect Analysis. 1991. Ferguson, Mo. 63135, USA, BIOSOFT.
8. Cochran, A. G. 2001. Protein-protein interfaces: mimics and inhibitors. Curr. Opin. Chem. Biol. 5:654-659.
9. Debnath, A. K., L. Radigan, and S. Jiang. 1999. Structure-based identification of small molecule antiviral compounds targeted to the gp41 core structure of the human immunodeciency virus type 1. J. Med. Chem. 42:3203-3209.
10. Dwyer, J. J., A. Hasan, K. L. Wilson, J. M. White, T. J. Matthews, and M. K. Delmedico. 2003. The hydrophobic pocket contributes to the structural stability of the N-terminal coiled coil of HIV gp41 but is not required for six-helix bundle formation. Biochemistry 42:4945-4953.
11. Eckert, D. M., V. N. Malashkevich, L. H. Hong, P. A. Carr, and P. S. Kim. 1999. Inhibiting HIV-1 entry: discovery of D-peptide inhibitors that target the gp41 coiled-coil pocket. Cell 99:103-115.
12. Ernst, J. T., O. Kutzki, A. K. Debnath, S. Jiang, H. Lu, and A. D. Hamilton. 2002. Design of a Protein Surface Antagonist Based on alpha-Helix Mimicry: Inhibition of gp41 Assembly and Viral Fusion thanks to the National Institutes of Health for support of this work and the Deutsche Forschungsgemeinschaft (DFG) for a research fellowship to O. K. Angew. Chem. Int. Ed Engl. 41:278-281.
13. Fauci, A. S. 2003. HIV and AIDS: 20 years of science. Nat. Med. 9:839-843.
14. Gadek, T. R. and J. B. Nicholas. 2003. Small molecule antagonists of proteins. Biochem. Pharmacol. 65:1-8.
15. He, Y., P. Agostino, and A. Pinter. 2003. Analysis of the immunogenic properties of single-chain polypeptide analogue of HIV-1 gp120-CD4 complex in transgenic mice that produce human immunoglobulins. Vaccine 21:4421-4429.
16. Hsu, M., J. M. Harouse, A. Gettie, C. Buckner, J. Blanchard, and C. Cheng-Mayer. 2003. Increased mucosal transmission but not enhanced pathogenicity of the CCR5-tropic, simian AIDS-inducing simian/human immunodeficiency virus SHIV(SF162P3) maps to envelope gp120. J. Virol. 77:989-998.
17. Huang, L., L. Zhang, and C. H. Chen. 2003. Potential Drug Targets on the HIV-1 Envelope Glycoproteins, gp120 and gp41. Curr. Pharm. Des 9:1453-1462.
18. Jiang, S., K. Lin, and A. R. Neurath. 1991. Enhancement of human immunodeficiency virus type-1 (HIV-1) infection by antisera to peptides from the envelope glycoproteins gp120/gp41. J. Exp. Med. 174: 1557-1563.
19. Jiang, S. and A. K. Debnath. 2000. A salt bridge between an N-terminal coiled coil of gp41 and an antiviral agent targeted to the gp41 core is important for anti-HIV-1 activity. Biochem. Biophys. Res. Commun. 270:153-157.
20. Jiang, S., K. Lin, and M. Lu. 1998. A conformation-specific monoclonal antibody reacting with fusion-active gp41 from the HIV-1 envelope glycoprotein. J. Virol. 72:10213-10217.
21. Jiang, S., K. Lin, N. Strick, and A. R. Neurath. 1993. HIV-1 inhibition by a peptide. Nature 365:113.
22. Jiang, S., K. Lin, N. Strick, and A. R. Neurath. 1993. Inhibition of HIV-1 infection by a fusion domain binding peptide from HIV-1 envelope glycoprotein gp41. Biochem. Biophys. Res. Commun. 195: 533-538.
23. Jiang, S., K. Lin, L. Zhang, and A. K. Debnath. 1999. A screening assay for antiviral compounds targeted to the HIV-1 gp41 core structure using a conformation-specific monoclonal antibody. J. Virol. Methods 80:85-96.
24. Jiang, S., L. Radigan, and L. Zhang. 2000. A convenient cell fusion assay for rapid screening for HIV entry inhibitors. Proc. SPIE 3926:212-219.
25. Jiang, S., Q. Zhao, and A. K. Debnath. 2002. Peptide and Non-peptide HIV Fusion Inhibitors. Curr. Pharm. Des. 8:563-580.
26. Kilby, J. M. and J. J. Eron. 2003. Novel therapies based on mechanisms of HIV-1 cell entry. N. Engl. J Med. 348:2228-2238.
27. Kilby, J. M., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag. 1998. Potent suppression of HIV-1 replication in humans by T-20, a peptide inhibitor of gp41-mediated virus entry. Nature Med. 4:1302-1307.
28. Kilby, J. M., J. P. Lalezari, J. J. Eron, M. Carlson, C. Cohen, R. C. Arduino, J. C. Goodgame, J. E. Gallant, P. Volberding, R. L. Murphy, F. Valentine, M. S. Saag, E. L. Nelson, P. R. Sista, and A. Dusek. 2002. The safety, plasma pharmacokinetics, and antiviral activity of subcutaneous enfuvirtide (T-20), a peptide inhibitor of gp41-mediated virus fusion, in HIV-infected adults. AIDS Res. Hum. Retroviruses 18:685-693.
29. Lalezari, J. P., K. Henry, M. O'Hearn, J. S. Montaner, P. J. Piliero, B. Trottier, S. Walmsley, C. Cohen, D. R. Kuritzkes, J. J. Eron, Jr., J. Chung, R. DeMasi, L. Donatacci, C. Drobnes, J. Delehanty, and M. Salgo. 2003. Enfuvirtide, an HIV-1 fusion inhibitor, for drug-resistant HIV infection in north and south America. N. Engl. J. Med. 348:2175-2185.
30. Lin, P. F., W. Blair, T. Wang, T. Spicer, Q. Guo, N. Zhou, Y. F. Gong, H. G. Wang, R. Rose, G. Yamanaka, B. Robinson, C. B. Li, R. Fridell, C. Deminie, G. Demers, Z. Yang, L. Zadjura, N. Meanwell, and R. Colonno. 2003. A small molecule HIV-1 inhibitor that targets the HIV-1 envelope and inhibits CD4 receptor binding. Proc. Natl. Acad. Sci. U.S.A 100:11013-11018.
31. Lipinski, C. A., F. Lombardo, B. W. Dominy, and P. J. Feeney. 2001. Experimental and computational approaches to estimate solubility and permeability in drug discovery and development settings. Advanced Drug Delivery Reviews 46:3-26.
32. Liu, S., Q. Zhao, and S. Jiang. 2003. Determination of the HIV-1 gp41 postfusion conformation modeled by synthetic peptides: applicable for identification of the HIV-1 fusion inhibitors. Peptide In press.
33. Lu, M., S. C. Blacklow, and P. S. Kim. 1995. A trimeric structural domain of the HIV-1 transmembrane glycoprotein. Nat. Struct. Biol. 2:1075-1082.
34. Lu, H., Q. Zhao, Z. Xu, and S. Jiang. 2003. Automatic quantitation of HIV-1 mediated cell-to-cell fusion with a digital image analysis system (DIAS): application for rapid screening of HIV-1 fusion inhibitors. J. Virol. Methods 107:155-161.
35. Lu, M. and P. S. Kim. 1997. A trimeric structural subdomain of the HIV-1 transmembrane glycoprotein. J. Biomol. Struct. Dyn. 15:465-471.
36. Matsuzaki, K., T. Ogino, T. Sunazuka, H. Tanaka, and S. Omura. 1997. Chloropeptins, new anti-HIV antibiotics inhibiting gp120-CD4 binding from Streptomyces sp. II. Structure elucidation of chloropeptin I. J. Antibiot. (Tokyo) 50:66-69.
37. McKnight, A., D. Wilkinson, G. Simmons, S. Talbot, L. Picard, M. Ahuja, M. Marsh, J. A. Hoxie, and P. R. Clapham. 1997. Inhibition of human immunodeficiency virus fusion by a monoclonal antibody to a coreceptor (CXCR4) is both cell type and virus strain dependent. J. Virol. 71:1692-1696.
38. Moore, J. P., B. A. Jameson, R. A. Weiss, and Q. J. Sattentau. 1993. The HIV-cell fusion reaction, p. 233-289. In J. Bentz (ed.), Viral Fusion Mechanisms. CRC Press, Boca Raton.
39. Murakami, T., T. Nakajima, Y. Koyanagi, K. Tachibana, N. Fujii, H. Tamamura, N. Yoshida, M. Waki, A. Matsumoto, O. Yoshie, T. Kishimoto, N. Yamamoto, and T. Nagasawa. 1997. A small molecule CXCR4 inhibitor that blocks T cell line-tropic HIV-1 infection. J. Exp. Med. 186:1389-1393.
40. Nakashima, H., M. Masuda, T. Murakami, Y. Koyanagi, A. Matsumoto, N. Fujii, and N. Yamamoto. 1992. Anti-human immunodeficiency virus activity of a novel synthetic peptide, T22 ([Tyr-5,12, Lys-7]polyphemusin II): a possible inhibitor of virus-cell fusion. Antimicrob. Agents. Chemother. 36:1249-1255.
41. Neurath, A. R., S. Jiang, N. Strick, K. Lin, Y. -Y. Li, and A. K. Debnath. 1996. Bovine β-lactoglobulin modified by 3-hydroxyphthalic anhydride blocks the CD4 cell receptors for HIV-1. Nature Med. 2:230-234.
42. Ockey, D. A. and T. R. Gadek. 2002. Inhibitors of protein-protein interactions. Expert. Opin. Ther. Pat. 12:393-400.
43. Pomerantz, R. J. and D. L. Horn. 2003. Twenty years of therapy for HIV-1 infection. Nat. Med. 9:867-873.
44. Prince, A. M., B. Horowitz, L. Baker, R. W. Shulman, H. Ralph, J. Valinsky, A. Cundell, B. Brotman, W. Boehle, F. Rey, and. 1988. Failure of a human immunodeficiency virus (HIV) immune globulin to protect chimpanzees against experimental challenge with HIV. Proc. Natl. Acad. Sci. U.S.A 85:6944-6948.
45. Sattentau, Q. J. and J. P. Moore. 1991. Conformational changes induced in the human immunodeficiency virus envelope glycoprotein by soluble CD4 binding. J. Exp. Med. 174:407-415.
46. Tan, K., J. Liu, J. Wang, S. Shen, and M. Liu. 1997. Atomic structure of a thermostable subdomain of HIV-1 gp41. Proc. Natl. Acad. Sci. 94: 12303-12308.
47. Toogood, P. L. 2002. Inhibition of protein-protein association by small molecules: approaches and progress. J Med. Chem 45:1543-1558.
48. Weissenhorn, W., A. Dessen, S. C. Harrison, J. J. Skehel, and D. C. Wiley. 1997. Atomic Structure of the Ectodomain from HIV-1 gp41. Nature 387:426-428.
49. Wild, C., T. Oas, C. McDanal, D. Bolognesi, and T. Matthews. 1992. A synthetic peptide inhibitor of human immunodeficiency virus replication: correlation between solution structure and viral inhibition. Proc. Natl. Acad. Sci. USA. 89: 10537-10541.
50. Wild, C. T., D. C. Shugars, T. K. Greenwell, C. B. McDanal, and T. J. Matthews. 1994. Peptides corresponding to a predictive alpha-helical domain of human immunodeficiency virus type 1 gp41 are potent inhibitors of virus infection. Proc. Natl. Acad. Sci. USA 91:9770-9774.
51. Zhao, Q., J. T. Ernst, A. D. Hamilton, A. K. Debnath, and S. Jiang. 2002. XTT formazan widely used to detect cell viability inhibits HIV type 1 infection in vitro by targeting gp41. AIDS Res. Hum. Retroviruses 18:989-997.
52. Zhao, Q., H. Lu, D. Schols, E. De Clercq, and S. Jiang. 2003. Development of a cell-based enzyme-linked immunosorbent assay for high throughput screening of human immunodeficiency virus type 1 entry inhibitors targeting the coreceptor CXCR4. AIDS Res. Hum. Retroviruses 19:947-955.

What is claimed is:

1. A method for inhibiting replication of human immunodeficiency virus in cells comprising contacting cells with an effective amount of a compound of the formula I, or its pharmaceutically acceptable salt and a pharmaceutically acceptable carrier, to inhibit the replication of the human immunodeficiency virus,

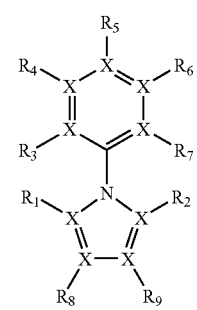

wherein X is C;
$R_1$ is selected from the group consisting of H and methyl;
$R_2$ is selected from the group consisting of H, methyl and phenyl;
$R_3$ is selected from the group consisting of H and methyl;
$R_4$ is selected from the group consisting of H, OH and COCH;
$R_5$ is selected from the group consisting of H, OH, Cl, COOCH$_3$ and COOH;
$R_6$ is selected from the group consisting of H, Cl and COOH;
$R_7$ is selected from the group consisting of H, OH and methyl;
$R_8$ is selected from the group consisting of H and CHO;
$R_9$ is H and at least one of $R_4$, $R_5$ and $R_6$ is COOH—.

2. The method of claim 1, further comprising contacting cells with an effective amount of an Acquired Immunodeficiency Syndrome (AIDS) treatment agent selected from the group consisting of anti-HIV agents, anti-infective agents, and immunomodulators.

3. A method for treating mammals infected with the human immunodeficiency virus, comprising administering to said mammals an effective amount of a compound of the formula I, or its pharmaceutically acceptable salt and a pharmaceutically acceptable carrier,

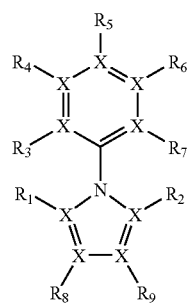

I wherein X is C;
R$_1$ is selected from the group consisting of H and methyl;
R$_2$ is selected from the group consisting of H, methyl and phenyl;
R$_3$ is selected from the group consisting of H and methyl;
R$_4$ is selected from the group consisting of H, OH and COOH;
R$_5$ is selected from the group consisting of H, OH, Cl, COOCH$_3$ and COOH;
R$_6$ is selected from the group consisting of H, Cl and COOH;
R$_7$ is selected from the group consisting of H, OH and methyl;
R$_8$ is selected from the group consisting of H and CHO;
R$_9$ is H and at least one of R$_4$, R$_5$ and R$_6$ is COOH—.

4. The method of claim 3, further comprising administering to said mammals an effective amount of an Acquired Immunodeficiency Syndrome (AIDS) treatment agent selected from the group consisting of anti-HIV agents, anti-infective agents, and immunomodulators.

5. A method for inhibiting replication of human immunodeficiency virus in cells comprising contacting cells with an effective amount of a compound of the formula I, or its pharmaceutically acceptable salt and a pharmaceutically acceptable carrier, to inhibit the replication of the human immunodeficiency virus,

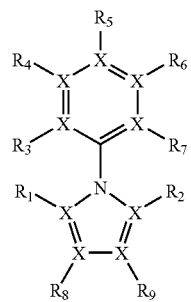

I wherein X is C, R$_4$ is COOH, and one of the following:
(a) R$_1$ is methyl, R$_2$ is phenyl, R$_5$ is OH, and each of R$_3$, R$_6$, R$_7$, R$_8$ and R$_9$ is H; or
(b) R$_1$ is methyl, R$_2$ is phenyl, R$_5$ is Cl, and each of R$_3$, R$_6$, R$_7$, R$_8$ and R$_9$ is H; or
(c) R$_1$ is methyl, R$_2$ is phenyl, and each of R$_3$, R$_5$, R$_6$, R$_7$, R$_8$ and R$_9$ is H; or
(d) R$_1$ and R$_2$ are each methyl, R$_5$ is OH, and each of R$_3$, R$_6$, R$_7$, R$_8$ and R$_9$ is H; or
(e) R$_5$ is Cl, and each of R$_1$, R$_2$, R$_3$, R$_6$, R$_7$, R$_8$ and R$_9$ is H; or
(f) R$_1$ and R$_2$ are each methyl, R$_6$ is COOH, and each of R$_3$, R$_5$, R$_7$, R$_8$ and R$_9$ is H; or
(g) R$_1$ and R$_2$ are each methyl, R$_7$ is OH, and each of R$_3$, R$_5$, R$_6$, R$_8$ and R$_9$ is H; or
(h) each of R$_1$, R$_2$, R$_3$, R$_5$, R$_6$, R$_7$, R$_8$ and R$_9$ is H.

6. The method of claim 5, further comprising contacting cells with an effective amount of an Acquired Immunodeficiency Syndrome (AIDS) treatment agent selected from the group consisting of anti-HIV agents, anti-infective agents, and immunomodulators.

7. A method for treating mammals infected with the human immunodeficiency virus, comprising administering to said mammals an effective amount of a compound of the formula I, or its pharmaceutically acceptable salt and a pharmaceutically acceptable carrier,

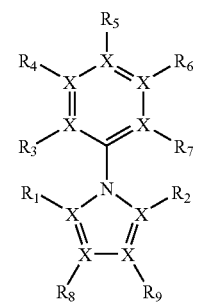

I wherein X is C, R$_4$ is COOH, and one of the following:
(a) R$_1$ is methyl, R$_2$ is phenyl, R$_5$ is OH, and each of R$_3$, R$_6$, R$_7$, R$_8$ and R$_9$ is H; or
(b) R$_1$ is methyl, R$_2$ is phenyl, R$_5$ is Cl, and each of R$_3$, R$_6$, R$_7$, R$_8$ and R$_9$ is H; or
(c) R$_1$ is methyl, R$_2$ is phenyl, and each of R$_3$, R$_5$, R$_6$, R$_7$, R$_8$ and R$_9$ is H; or
(d) R$_1$ and R$_2$ are each methyl, R$_5$ is OH, and each of R$_3$, R$_6$, R$_7$, R$_8$ and R$_9$ is H; or
(e) R$_5$ is Cl, and each of R$_1$, R$_2$, R$_3$, R$_6$, R$_7$, R$_8$ and R$_9$ is H; or
(f) R$_1$ and R$_2$ are each methyl, R$_6$ is COOH, and each of R$_3$, R$_5$, R$_7$, R$_8$ and R$_9$ is H; or
(g) R$_1$ and R$_2$ are each methyl, R$_7$ is OH, and each of R$_3$, R$_5$, R$_6$, R$_8$ and R$_9$ is H; or
(h) each of R$_1$, R$_2$, R$_3$, R$_5$, R$_6$, R$_7$, R$_8$ and R$_9$ is H.

8. The method of claim 7, further comprising administering to said mammals an effective amount of an Acquired Immunodeficiency Syndrome (AIDS) treatment agent selected from the group consisting of anti-HTV agents, anti-infective agents, and immunomodulators.

9. A method for inhibiting replication of human immunodeficiency virus in cells comprising contacting cells with an effective amount of a compound of the formula I, or its pharmaceutically acceptable salt and a pharmaceutically acceptable carrier, to inhibit the replication of the human immunodeficiency virus,

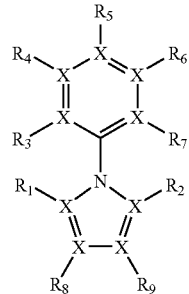

wherein X is C, $R_1$ and $R_2$ are each methyl, $R_5$ is COOH, and one of the following:
- (a) $R_4$ is OH, and each of $R_3$, $R_6$, $R_7$, $R_8$ and $R_9$ is H; or
- (b) $R_6$ is Cl, and each of $R_3$, $R_4$, $R_7$, $R_8$ and $R_9$ is H; or
- (c) each of $R_3$, $R_4$, $R_6$, $R_7$, $R_8$ and $R_9$ is H; or
- (d) $R_6$ is Cl, $R_8$ is CHO, and each of $R_3$, $R_4$, $R_7$ and $R_9$ is H; or
- (e) $R_7$ is OH, and each of $R_3$, $R_4$, $R_6$, $R_8$ and $R_9$ is H; or
- (f) $R_7$ is methyl, and each of $R_3$, $R_4$, $R_6$, $R_8$ and $R_9$ is H; or
- (g) $R_8$ is CHO, and each of $R_3$, $R_4$, $R_6$, $R_7$, and $R_9$ is H.

10. The method of claim 9, further comprising contacting cells with an effective amount of an Acquired Immunodeficiency Syndrome (AIDS) treatment agent selected from the group consisting of anti-HIV agents, anti-infective agents, and immunomodulators.

11. A method for treating mammals infected with the human immunodeficiency virus, comprising administering to said mammals an effective amount of a compound of the formula I, or its pharmaceutically acceptable salt and a pharmaceutically acceptable carrier,

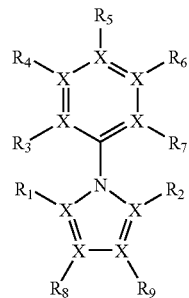

wherein X is C, $R_1$ and $R_2$ are each methyl, $R_5$ is COCH, and one of the following:
- (a) $R_4$ is OH, and each of $R_3$, $R_6$, $R_7$, $R_8$ and $R_9$ is H; or
- (b) $R_6$ is Cl, and each of $R_3$, $R_4$, $R_7$, $R_8$ and $R_9$ is H; or
- (c) each of $R_3$, $R_4$, $R_6$, $R_7$, $R_8$ and $R_9$ is H; or
- (d) $R_6$ is Cl, $R_8$ is CHO, and each of $R_3$, $R_4$, $R_7$ and $R_9$ is H; or
- (e) $R_7$ is OH, and each of $R_3$, $R_4$, $R_6$, $R_8$ and $R_9$ is H; or
- (f) $R_7$ is methyl, and each of $R_3$, $R_4$, $R_6$, $R_8$ and $R_9$ is H; or
- (g) $R_8$ is CHO, and each of $R_3$, $R_4$, $R_6$, $R_7$ and $R_9$ is H.

12. The method of claim 11, further comprising administering to said mammals an effective amount of an Acquired Immunodeficiency Syndrome (AIDS) treatment agent selected from the group consisting of anti-HIV agents, anti-infective agents, and immunomodulators.

13. A method for inhibiting replication of human immunodeficiency virus in cells comprising contacting cells with an effective amount of a compound of the formula I, or its pharmaceutically acceptable salt and a pharmaceutically acceptable carrier, to inhibit the replication of the human immunodeficiency virus,

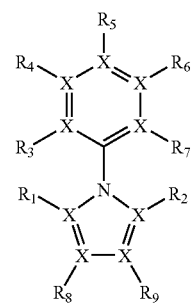

wherein X is C, $R_6$ is COOH, and one of the following:
- (a) $R_1$, $R_2$ and $R_7$ are each methyl, and each of $R_3$, $R_4$, $R_5$, $R_8$ and $R_9$ is H; or
- (b) $R_1$ and $R_2$ are each methyl, and each of $R_3$, $R_4$, $R_5$, $R_7$, $R_8$ and $R_9$ is H; or
- (c) $R_7$ is methyl, and each of $R_1$, $R_2$, $R_3$, $R_4$, $R_5$, $R_8$ and $R_9$ is H; or
- (d) $R_1$ and $R_2$ are each methyl, $R_5$ is Cl, and each of $R_3$, $R_4$, $R_7$, $R_8$ and $R_9$ is H; or
- (e) $R_1$, $R_2$ and $R_3$ are each methyl, and each of $R_4$, $R_5$, $R_7$, $R_8$ and $R_9$ is H.

14. The method of claim 13, further comprising contacting cells with an effective amount of an Acquired Immunodeficiency Syndrome (AIDS) treatment agent selected from the group consisting of anti-HIV agents, anti-infective agents, and immunomodulators.

15. A method for treating mammals infected with the human immunodeficiency virus, comprising administering to said mammals an effective amount of a compound of the formula I, or its pharmaceutically acceptable salt and a pharmaceutically acceptable carrier,

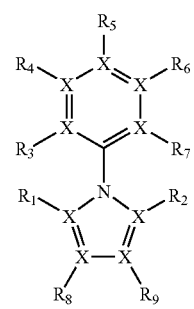

wherein X is C, $R_6$ is COCH, and one of the following:
- (a) $R_1$, $R_2$ and $R_7$ are each methyl, and each of $R_3$, $R_4$, $R_5$, $R_8$ and $R_9$ is H; or (b) $R_1$ and $R_2$ are each methyl, and each of $R_3$, $R_4$, $R_5$, $R_7$, $R_8$ and $R_9$ is H; or (c) $R_7$ is methyl, and each of $R_1$, $R_2$, $R_3$, $R_4$, $R_5$, $R_8$ and $R_9$ is H; or (d) $R_1$ and $R_2$ are each methyl, $R_5$ is Cl, and each of $R_3$, $R_4$, $R_7$, $R_8$ and $R_9$ is H; or (e) $R_1$, $R_2$ and $R_3$ are each methyl, and each of $R_4$, $R_5$, $R_7$, $R_8$ and $R_9$ is H.

16. The method of claim 15, further comprising administering to said mammals an effective amount of an Acquired Immunodeficiency Syndrome (AIDS) treatment agent selected from the group consisting of anti-HIV agents, anti-infective agents, and immunomodulators.

17. A compound of the formula I, or a pharmaceutically acceptable salt thereof,

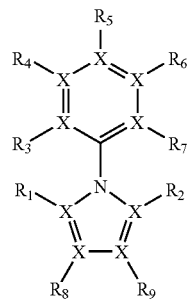

I wherein X is C; $R_1$ and $R_2$ are $CH_3$; $R_3$ is H; $R_4$ is OH; $R_5$ is COOH; and $R_6$, $R_7$, $R_8$ and $R_9$ are each H.

18. A pharmaceutical composition comprising an effective amount of the compound of claim 17.

19. A method for inhibiting replication of human immunodeficiency virus in cells, comprising contacting the cells with the pharmaceutical composition of claim 18.

20. The method of claim 19, further comprising contacting cells with an effective amount of an Acquired Immunodeficiency Syndrome (AIDS) treatment agent selected from the group consisting of anti-HIV agents, anti-infective agents, and immunomodulators.

21. A method for treating mammals infected with the human immunodeficiency virus, or treatment of Acquired Immunodeficiency Syndrome (AIDS) in a subject, comprising administering to said mammals or subject the pharmaceutical composition of claim 18.

22. The method of claim 21, further comprising administering to said mammals or subject an effective amount of an Acquired Immunodeficiency Syndrome (AIDS) treatment agent selected from the group consisting of anti-HIV agents, anti-infective agents, and immunomodulators.

23. A method for inhibiting replication of human immunodeficiency virus in cells comprising contacting cells with an effective amount of a compound of the formula I, or its pharmaceutically acceptable salt and a pharmaceutically acceptable carrier, to inhibit the replication of the human immunodeficiency virus,

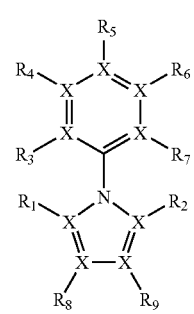

I wherein X is C; $R_1$, $R_2$ and $R_3$ are each H; $R_4$ is COOH; $R_5$ is Cl; and $R_6$, $R_7$, $R_8$ and $R_9$ are each H.

24. The method of claim 23, further comprising contacting cells with an effective amount of an Acquired Immunodeficiency Syndrome (AIDS) treatment agent selected from the group consisting of anti-HIV agents, anti-infective agents, and immunomodulators.

25. A method for treating mammals infected with the human immunodeficiency virus, comprising administering to said mammals an effective amount of a compound of the formula I, or its pharmaceutically acceptable salt and a pharmaceutically acceptable carrier,

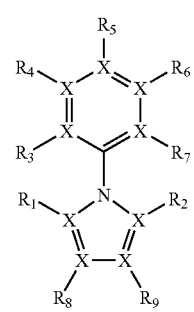

I wherein X is C; $R_1$, $R_2$ and $R_3$ are each H; $R_4$ is COCH; $R_5$ is Cl; and $R_6$, $R_7$, $R_8$ and $R_9$ are each H.

26. The method of claim 25, further comprising administering to said mammals an effective amount of an Acquired Immunodeficiency Syndrome (AIDS) treatment agent selected from the group consisting of anti-HIV agents, anti-infective agents, and immunomodulators.

* * * * *

UNITED STATES PATENT AND TRADEMARK OFFICE
CERTIFICATE OF CORRECTION

PATENT NO. : 7,241,803 B2
APPLICATION NO. : 10/706027
DATED : July 10, 2007
INVENTOR(S) : Jiang et al.

It is certified that error appears in the above-identified patent and that said Letters Patent is hereby corrected as shown below:

On page 2, first publication, "Peptide in press" should be -- Peptide 24:1303-1313. --

Figure 2: the orientation of the y-axis label should be reversed, as shown.

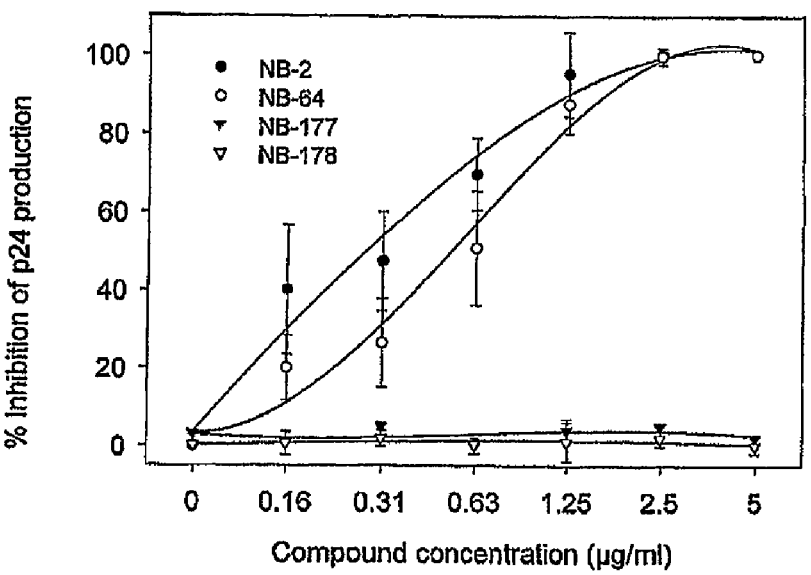

Figure 4: the orientation of the y-axis label should be reversed, as shown.

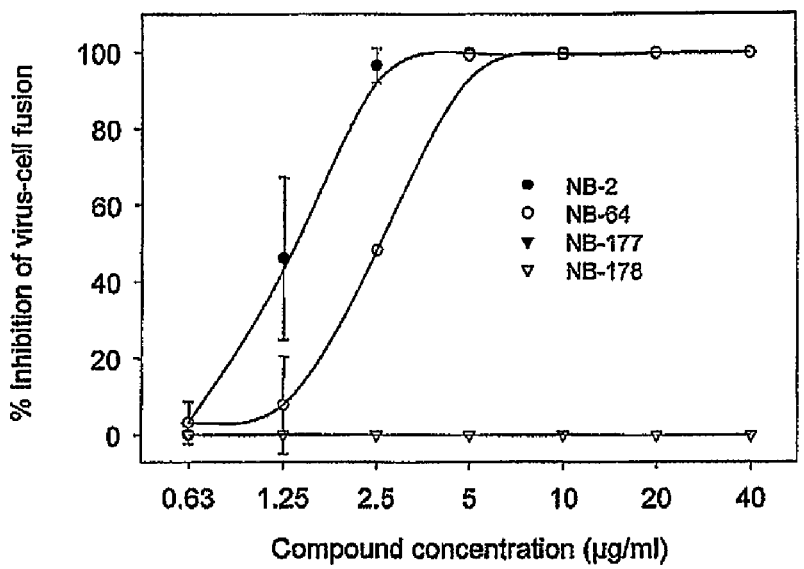

UNITED STATES PATENT AND TRADEMARK OFFICE
CERTIFICATE OF CORRECTION

PATENT NO. : 7,241,803 B2
APPLICATION NO. : 10/706027
DATED : July 10, 2007
INVENTOR(S) : Jiang et al.

It is certified that error appears in the above-identified patent and that said Letters Patent is hereby corrected as shown below:

Figure 4 (continued)

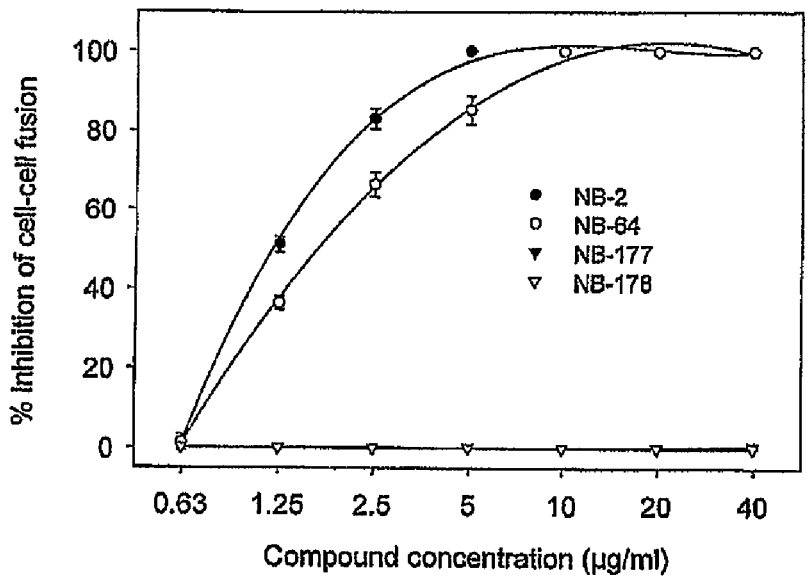

Figure 6: the orientation of the y-axis label should be reversed, as shown.

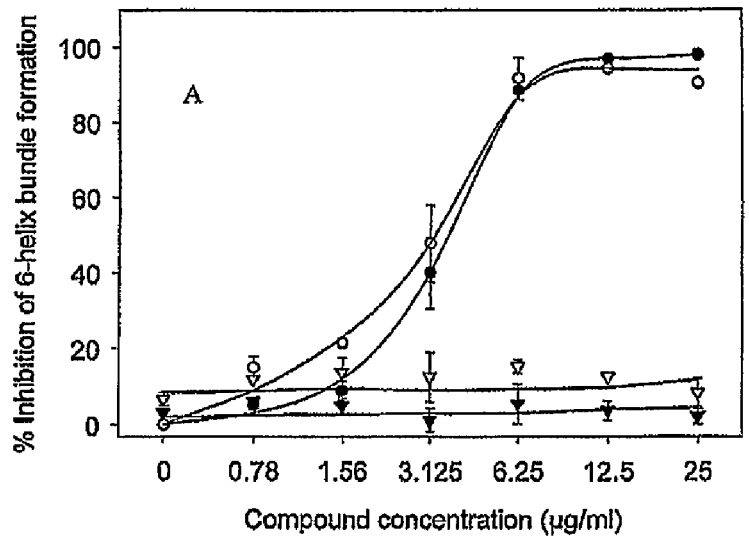

UNITED STATES PATENT AND TRADEMARK OFFICE
CERTIFICATE OF CORRECTION

PATENT NO.         : 7,241,803 B2                                    Page 3 of 4
APPLICATION NO. : 10/706027
DATED              : July 10, 2007
INVENTOR(S)        : Jiang et al.

It is certified that error appears in the above-identified patent and that said Letters Patent is hereby corrected as shown below:

Figure 8: the orientation of the y-axis label should be reversed, as shown.

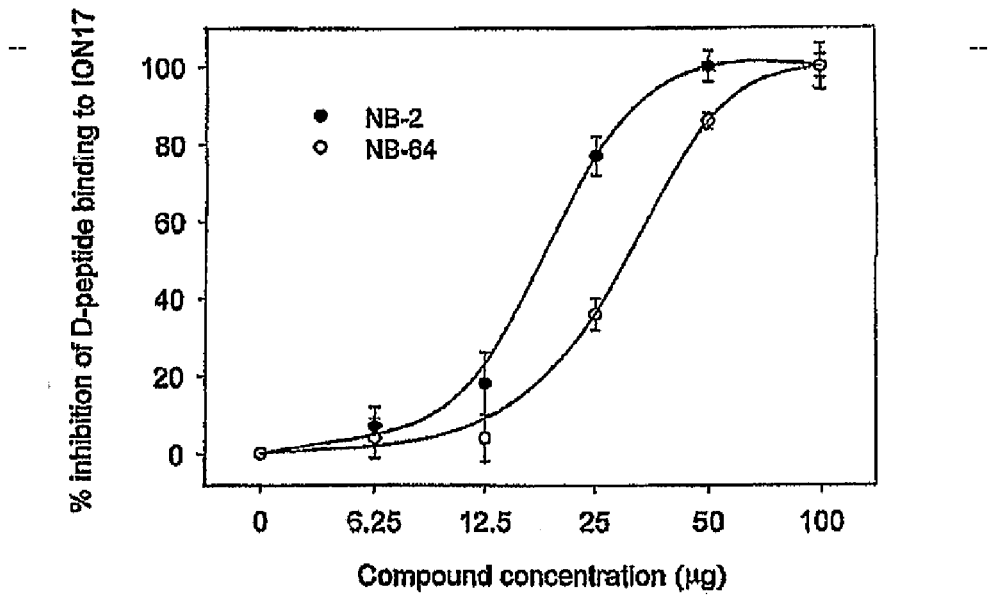

In column 21, reference 32, "Peptide in press" should be --Peptide 24:1303-1313. --

In column 22, line 57, "COCH" should be -- COOH --

In column 22, line 65, "R9 is H" should be -- R9 is H; --

In column 22, line 65, "COOH-" should be -- COOH --

In column 23, line 39, "R9 is H" should be -- R9 is H; --

In column 23, line 39, "COOH—" should be -- COOH --

In column 23, line 39, "R9" should be aligned with "R8" of line 38

In column 24, line 1, "COON" should be -- COOH --

In column 25, line 56, "COCH" should be -- COOH --

In column 26, line 65, "COCH" should be -- COOH --

UNITED STATES PATENT AND TRADEMARK OFFICE
CERTIFICATE OF CORRECTION

PATENT NO. : 7,241,803 B2
APPLICATION NO. : 10/706027
DATED : July 10, 2007
INVENTOR(S) : Jiang et al.

It is certified that error appears in the above-identified patent and that said Letters Patent is hereby corrected as shown below:

In column 28, line 48, "COCH" should be -- COOH --

Signed and Sealed this

Thirtieth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,241,803 B2
APPLICATION NO. : 10/706027
DATED : July 10, 2007
INVENTOR(S) : Shibo Jiang and Asim Kumar Debnath It is certified that error appears in the above-identified patent and that said Letters Patent is hereby corrected as shown below:

Column 1, line 9, "Government may have" should be changed to --Government has--.

Signed and Sealed this
Twenty-fourth Day of July, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,241,803 B2 |
| APPLICATION NO. | : 10/706027 |
| DATED | : July 10, 2007 |
| INVENTOR(S) | : Shibo Jiang et al. |

It is certified that error appears in the above-identified patent and that said Letters Patent is hereby corrected as shown below:

In the Specification

Column 1, lines 7 - 10, remove the text reading "The invention disclosed herein was supported in part by National Institute of Health Grant ROI AI46221. Accordingly, the United States Government may have certain rights in this invention." and add --This invention was made with government support under Grant RO1 AI46221 awarded by the National Institute of Health. The government has certain rights in the invention.--.

Signed and Sealed this
Twenty-sixth Day of January, 2016

Michelle K. Lee
*Director of the United States Patent and Trademark Office*